United States Patent [19]

Freyne et al.

[11] Patent Number: 5,220,023

[45] Date of Patent: Jun. 15, 1993

[54] GLYCINE DERIVATIVES

[75] Inventors: Eddy J. E. Freyne, Rumst; Alfons H. M. Raeymaekers, Beerse, both of Belgium

[73] Assignee: Janssen Pharmaceutica N.V., Beerse, Belgium

[21] Appl. No.: 866,704

[22] Filed: Apr. 10, 1992

Related U.S. Application Data

[60] Division of Ser. No. 735,229, Jul. 24, 1991, Pat. No. 5,120,845, which is a division of Ser. No. 615,748, Nov. 16, 1990, Pat. No. 5,043,327, which is a continuation-in-part of Ser. No. 529,826, May 29, 1990, abandoned, which is a continuation-in-part of Ser. No. 463,922, Jan. 9, 1990, abandoned, which is a continuation-in-part of Ser. No. 381,338, Jul. 18, 1989, abandoned.

[51] Int. Cl.$^5$ ............... C07C 219/04; C07D 295/192
[52] U.S. Cl. .................................. 544/165; 549/77; 560/38; 562/440; 562/443

[58] Field of Search ................ 544/165; 560/38; 549/77; 562/440, 443

[56] References Cited

U.S. PATENT DOCUMENTS 2,642,456  6/1953  Emerson et al. .................. 560/38

FOREIGN PATENT DOCUMENTS 798097  1/1981  U.S.S.R. .

*Primary Examiner*—Robert W. Ramsuer
*Attorney, Agent, or Firm*—Charles J. Metz

[57] ABSTRACT

The present invention relates to novel positive inotropic and lusitropic 3,5-dihydroimidazo[2,1-b]quinazolin-2(1H)-one derivatives having positive inotropic and lusitropic properties which are useful in the treatment of warm-blooded animals suffering from Congestive Heart Failure. Pharmaceutical compositions containing said compounds as an active ingredient. Methods of preparing said compounds and pharmaceutical compositions.

1 Claim, No Drawings

GLYCINE DERIVATIVES

This application is a division of application Ser. No. 735,229, filed Jul. 24, 1991, now U.S. Pat. No. 5,120,845, which was a division of application Ser. No. 615,748, filed on Nov. 16, 1990, now U.S. Pat. No. 5,043,327, which was a continuation-in-part of application Ser. No. 529,826, filed May 29, 1990, now abandoned, which was a continuation-in-part of application Ser. No. 463,922, filed Jan. 9, 1990, now abandoned, which in turn was a continuation-in-part of application Ser. No. 381,338, filed Jul. 18, 1989, now abandoned.

BACKGROUND OF THE INVENTION

In EP-A-O,116,948, EP-A-O,153,152 and in U.S. Pat. Nos. 4,593,029 and 4,670,434 there are described a number of imidazo[2,1-b]quinazolinones as phosphodiesterase inhibitors having positive inotropic properties. Analogous compounds are also disclosed in J. Med. Chem., 30, pp. 303–318 (1987) and 31, pp. 145–152 (1988).

DESCRIPTION OF THE INVENTION

The present invention is concerned with novel 3,5-dihydroimidazo[2,1-b]quinazolin-2(1H)-one derivatives having the formula

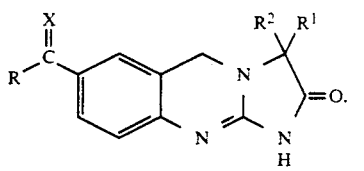

the pharmaceutically acceptable addition salts thereof and the stereochemically isomeric forms thereof, wherein R is hydrogen, $C_{1-6}$alkyl, phenyl optionally substituted with from 1 to 3 substituents each independently selected from halo, hydroxy, $C_{1-6}$alkyloxy, $C_{1-6}$alkyl or trifluoromethyl; pyridinyl; or thienyl optionally substituted with halo or $C_{1-6}$alkyl;

$R^1$ is hydrogen or $C_{1-6}$alkyl;

$R^2$ is hydrogen, $C_{1-6}$alkyl, hydroxy$C_{1-6}$alkyl or phenyl; or $R^1$ and $R^2$ taken together may also form a $C_{1-5}$alkanediyl radical;

X is a radical of formula $$=O \qquad (a),$$

$$=N-O-R^3 \qquad (b),$$

or $$=CH-R^4 \qquad (c);$$

$R^3$ is hydrogen, tri($C_{1-6}$alkyl)silyl or $C_{1-6}$alkyl optionally substituted with COOH, COO$C_{1-4}$alkyl, CONR$^5$R$^6$ or COOCH$_2$CONR$^7$R$^8$;

$R^4$ is COOH, COO$C_{1-4}$alkyl, CONR$^5$R$^6$, COOCH$_2$CONR$^7$R$^8$ or $C_{1-6}$alkyl optionally substituted with COOH, COO$C_{1-4}$alkyl, CONR$^5$R$^6$ or COOCH$_2$CONR$^7$R$^8$;

$R^5$ is hydrogen, $C_{1-4}$alkyl, hydroxy$C_{1-4}$alkyl, $C_{1-4}$alkyloxy$C_{1-4}$alkyl, hydroxycarbonyl$C_{1-4}$alkyl, $C_{1-4}$alkyloxycarbonyl$C_{1-4}$alkyl;

$R^6$ is hydrogen, $C_{1-4}$alkyl, hydroxy$C_{1-4}$alkyl or $C_{3-7}$cycloalkyl; or $R^5$ and $R^6$ taken together with the nitrogen atom to which they are attached may form a pyrrolidinyl, morpholinyl or piperazinyl ring, said piperazinyl ring being optionally substituted on the nitrogen atom with $C_{1-4}$alkyl or hydroxy$C_{1-4}$alkyl; and $R^7$ and $R^8$ each independently are hydrogen, $C_{1-4}$alkyl or hydroxy$C_{1-4}$alkyl.

In the foregoing definitions the term halo defines fluoro, chloro, bromo and iodo; $C_{1-4}$alkyl defines straight and branched saturated hydrocarbon radicals having from 1 to 4 carbon atoms, such as, for example, methyl, ethyl, propyl, 1-methylethyl, butyl, 1-methylpropyl, 2-methylpropyl and 1,1-dimethylethyl; $C_{1-6}$alkyl defines $C_{1-4}$alkyl and the higher homologs thereof such as, for example, pentyl, hexyl and the like; $C_{3-7}$cycloalkyl defines cyclopropyl, cyclobutyl, cyclopentyl, cyclohexyl and cycloheptyl; $C_{1-5}$alkanediyl defines straight and branch chained bivalent hydrocarbon radicals having from 1 to 5 carbon atoms such as, for example, methylene, 1,2-ethanediyl, 1,3-propanediyl, 1,4-butanediyl, 1,5-pentanediyl, 1,1-ethanediyl, 1,1-propanediyl, 1,2-propanediyl and the like. Tri($C_{1-6}$alkyl)silyl in particular may be trimethylsilyl, triethylsilyl, tert.butyldimethylsilyl and the like.

Pharmaceutically acceptable addition salts as mentioned hereinabove comprise the therapeutically active non-toxic addition salt forms which the compounds of formula (I) are able to form. Said salt forms can conveniently be obtained by treating the base form of the compounds of formula (I) with appropriate acids such as inorganic acids, for example, hydrohalic acid, e.g. hydrochloric, hydrobromic and the like acids, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) containing acidic protons may also be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt also comprises the hydrates and solvent addition forms which the compounds of formula (I) are able to form. Examples of such forms are e.g. hydrates, alcoholates and the like.

The compounds of this invention may have several asymmetric carbon atoms in their structure. Each of these chiral centers may be indicated by the stereochemical descriptors R and S. The compounds of formula (I) wherein X is a radical of formula (b) or (c) may occur as mixtures of E- and Z-forms or as pure E-forms or pure Z-forms. This R and S notation and E and Z notation corresponds to the rules described in Pure Appl. Chem., 1976, 45, 11–30.

Pure stereochemically isomeric forms of the compounds of formula (I) may be obtained by the application of art-known procedures. Diastereoisomers may be separated by physical methods such as selective crystallization and chromatographic techniques, e.g. counter current distribution, liquid chromatography and the like; and enantiomers may be separated from each other following art-known resolution methods, for example, by the selective crystallization of their diastereomeric salts with chiral acids. Pure stereochemically isomeric forms may also be derived from the corresponding pure stereochemically isomeric forms of the appropriate starting materials, provided that the reactions occur stereospecifically. Preferably, if a specific stereoisomer is desired, said compound will be synthesized by stereo-specific methods of preparation. These methods will advantageously employ enantiomerically pure starting materials. Stereochemically isomeric forms of the compounds of formula (I) are obviously intended to be included within the scope of the invention.

A first group of interesting compounds are those compounds of formula (I) wherein $R^2$ is hydrogen, $C_{1-6}$alkyl or hydroxy$C_{1-6}$alkyl; and/or $R^1$ and $R^2$ taken together may also form a $C_{1-5}$alkanediyl radical; and/or R is phenyl optionally substituted with from 1 to 3 substituents each independently selected from halo, hydroxy, $C_{1-6}$alkyloxy, $C_{1-6}$alkyl or trifluoromethyl.

A second group of interesting compounds are those compounds of formula (I) wherein $R^2$ is hydrogen, $C_{1-6}$alkyl or hydroxy$C_{1-6}$alkyl; and/or $R^1$ and $R^2$ taken together may also form a $C_{1-5}$alkanediyl radical; and/or R is hydrogen, $C_{1-6}$alkyl or pyridinyl.

A third group of interesting compounds are those compounds of formula (I) wherein $R^2$ is hydrogen, $C_{1-6}$alkyl or hydroxy$C_{1-6}$alkyl; and/or $R^1$ and $R^2$ taken together may also form a $C_{1-5}$alkanediyl radical; and/or R is thienyl.

More interesting compounds are those interesting compounds wherein $R^1$ is hydrogen; and/or $R^2$ is hydrogen or $C_{1-6}$alkyl; and/or R is phenyl optionally substituted with halo, $C_{1-6}$alkyloxy or $C_{1-6}$alkyl; and/or X is a radical of formula (a), (b) or (c); and/or $R^5$ is hydrogen or $C_{1-4}$alkyl; and/or $R^6$ is $C_{1-4}$alkyl or $C_{3-7}$cycloalkyl.

Other more interesting compounds are those interesting compounds wherein $R^1$ is hydrogen; and/or $R^2$ is hydrogen or $C_{1-6}$alkyl; and/or R is hydrogen, $C_{1-6}$alkyl or pyridinyl; and/or X is a radical of formula (a), (b) or (c); and/or $R^5$ is hydrogen or $C_{1-4}$alkyl; and/or $R^6$ is $C_{1-4}$alkyl or $C_{3-7}$cycloalkyl.

Still other more interesting compounds are those interesting compounds wherein $R^1$ is hydrogen; and/or $R^2$ is hydrogen or $C_{1-6}$alkyl; and/or R is thienyl; and/or X is a radical of formula (a), (b) or (c); and/or $R^5$ is hydrogen or $C_{1-4}$alkyl; and/or $R^6$ is $C_{1-4}$alkyl or $C_{3-7}$cycloalkyl.

Particularly interesting compounds are those interesting compounds wherein $R^1$ and $R^2$ are hydrogen; and/or R is phenyl optionally substituted with fluoro, chloro, bromo, methoxy or methyl; and/or X is a radical of formula (a), (b) or (c); and/or $R^3$ is hydrogen, $C_{1-4}$alkyl substituted with $COOC_{1-4}$alkyl or with $CONR^5R^6$, $R^5$ being $C_{1-4}$alkyl and $R^6$ being $C_{5-7}$cycloalkyl; and/or $R^4$ is COOH, $COOC_{1-4}$alkyl or $CONR^5R^6$, $R^5$ being $C_{1-4}$alkyl and $R^6$ being $C_{5-7}$cycloalkyl.

Other particularly interesting compounds are those interesting compounds wherein $R^1$ and $R^2$ are hydrogen; and/or R is hydrogen, $C_{1-4}$alkyl or pyridinyl; and/or X is a radical of formula (a), (b) or (c); and/or $R^3$ is hydrogen, $C_{1-4}$alkyl substituted with $COOC_{1-4}$alkyl or with $CONR^5R^6$, $R^5$ being $C_{1-4}$alkyl and $R^6$ being $C_{5-7}$cycloalkyl; and/or $R^4$ is COOH, $COOC_{1-4}$alkyl or $CONR^5R^6$, $R^5$ being $C_{1-4}$alkyl and $R^6$ being $C_{5-7}$cycloalkyl.

Still other particularly interesting compounds are those interesting compounds wherein $R^1$ and $R^2$ are hydrogen; and/or R is thienyl; and/or X is a radical of formula (a), (b) or (c); and/or $R^3$ is hydrogen, $C_{1-4}$alkyl substituted with $COOC_{1-4}$alkyl or with $CONR^5R^6$, $R^5$ being $C_{1-4}$alkyl and $R^6$ being $C_{5-7}$cycloalkyl; and/or $R^4$ is COOH, $COOC_{1-4}$alkyl or $CONR^5R^6$, $R^5$ being $C_{1-4}$alkyl and $R^6$ being $C_{5-7}$cycloalkyl.

The most interesting compounds within the present invention are:
(E+Z)-3,5-dihydro-7-[(hydroxyimino)phenylmethyl]imidazo[2,1-b]quinazolin-2(1H)-one,
(E)-N-cyclohexyl-N-methyl-2-[[[phenyl-(1,2,3,5-tetrahydro-2-oxoimidazo[2,1-b]-quinazolin-7-yl)methylene]oxy]acetamide,
(E)-3,5-dihydro-7-[(hydroxyimino)phenylmethyl]imidazo[2,1-b]quinazolin-2(1H)-one,
(E)-N-cyclohexyl-N-methyl-2-[[[(1,2,3,5-tetrahydro-2-oxoimidazo[2,1-b]quinazolin-7-yl)methylene]amino]oxy]acetamide and
(E+Z)-N-cyclohexyl-N-methyl-2-[[[(1,2,3,5-tetrahydro-2-oxoimidazo[2,1-b]quinazolin-7-yl)(2-thienyl)methylene]amino]oxy]acetamide, the pharmaceutically acceptable addition salts and the stereochemically isomeric forms thereof.

In order to simplify the structural representation of the compounds and of some of the intermediates in the following preparations, the 3,5-dihydro-imidazo[2,1-b]quinazolin-2(1H)-one moiety will hereinafter be represented by the symbol D.

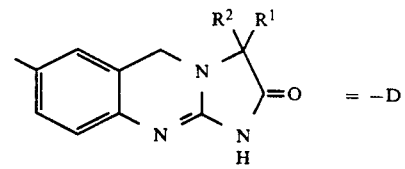

The compounds of formula (I) can generally be prepared by cyclizing an intermediate of formula (II) with a reagent of formula (III) wherein $W^1$ represents a leaving group such as, for example, trihalomethyl, e.g. trichloromethyl or a halide, in particular bromide, in a suitable solvent.

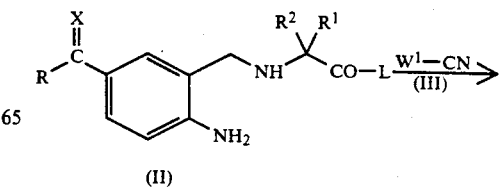

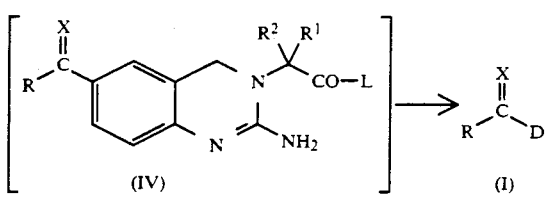

In formulae (II) and (IV) L represents a reactive leaving group such as, for example, $C_{1-6}$alkyloxy, phenyloxy, hydroxy, amino, imidazolyl and the like. Suitable solvents for said cyclization are, for example, water; aromatic hydrocarbons, e.g. benzene, methylbenzene, dimethylbenzene and the like; alcohols, e.g. methanol, ethanol, 1-propanol, 2-propanol, 1-butanol and the like, diols, e.g. 1,2-ethanediol and the like; dipolar aprotic solvents, e.g. N,N-dimethylformamide, N,N-dimethylacetamide, hexamethylphosphor triamide and the like; ethers, e.g. tetrahydrofuran, 1,1'-oxybisethane, 1,4-dioxane and the like; halogenated hydrocarbons, e.g. trichloromethane, tetrachloromethane and the like; and mixtures thereof. The reaction can conveniently be conducted by stirring the reactants initially at a low temperature such as between $-10°$ C. and $5°$ C. and then at room temperature. In some instances the intermediate guanidine of formula (IV) may be isolated at this stage. In order to enhance the reaction rate of the second cyclization step it may be appropriate to heat the reaction mixture at an elevated temperature, in particular at the reflux temperature of the reaction mixture.

The compounds of formula (I) may also be obtained by cyclizing an intermediate of formula (II) with N-cyanoimido-S,S-dimethyldithiocarbonate or with an Q-alkylisourea or S-alkylisothiourea wherein $R^9$ is alkyl, thus yielding respectively a N-cyanoguanidine of formula (IV-a) or a N-alkyloxycarbonyl guanidine of formula (IV-b).

cyclization in the presence of an acid, optionally at an enhanced temperature.

In all of the foregoing and in the following preparations, the reaction products may be isolated from the reaction mixture and, if necessary, further purified according to methodologies generally known in the art.

The compounds of formula (I) can also be prepared from a quinazoline derivative of formula (V) wherein L is a leaving group as defined hereinbefore and $R^9$ is $C_{1-6}$alkyl or aryl,

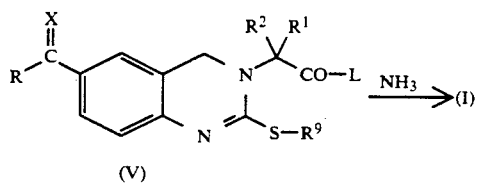

by cyclization with ammonia or a salt thereof such as, for example, an ammonium halide, e.g. ammonium chloride; ammonium carbonate; ammonium acetate and the like ammonium salts, in a suitable reaction-inert solvent such as, for example, water, an alkanol, e.g. methanol, ethanol and the like, a carboxylic acid, e.g. acetic, propanoic acid and the like, or a mixture of such solvents. In order to enhance the rate of the reaction, it may be advantageous to heat the reaction mixture, in particular to the reflux temperature of the reaction mixture.

The compounds of formula (I) wherein X is a radical of formula (b), said compounds being represented by formula (I-b), can be obtained by reacting a compound of formula (I) wherein X is a radical of formula (a), said compound being represented by formula (I-a), with an appropriate hydroxylamine derivative of formula (VI) or an acid addition salt thereof.

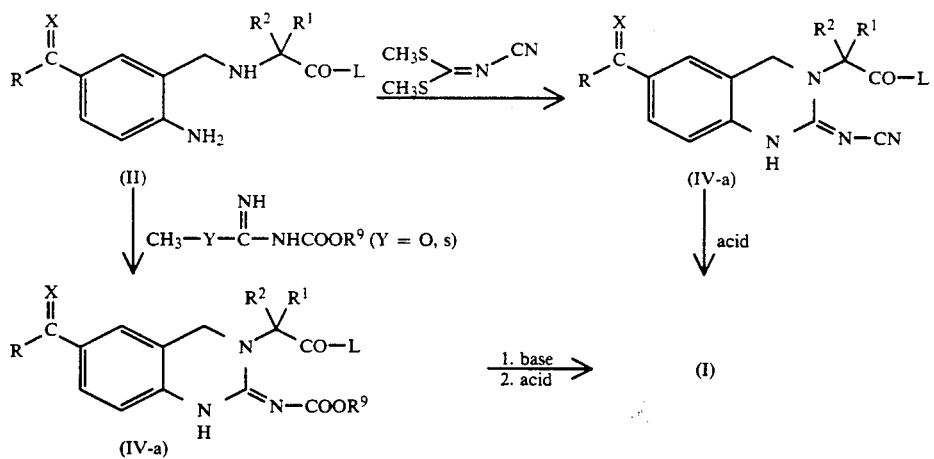

The N-cyanoguanidine of formula (IV-a) may be converted into compounds of formula (I) upon heating, preferably at the reflux temperature of the reaction mixture, in a suitable solvent such as an alkanol, e.g. ethanol, propanol, butanol and the like, and in the presence of an acid such as, for example, hydrochloric acid. The N-alkyloxycarbonyl guanidine of formula (IV-b) in turn, may be converted into compounds of formula (I) by base hydrolysis of the carbamate and subsequent

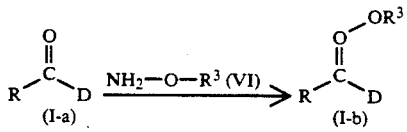

Said reaction can be carried out by stirring and heating the reagents in an appropriate solvent at an enhanced temperature, in particular the reflux temperature of the reaction mixture. Appropriate solvents are for example, aromatic hydrocarbons, e.g. benzene, methylbenzene, dimethylbenzene and the like; halogenated hydrocarbons, e.g. trichloromethane, tetrachloromethane and the like; ethers, e.g. 1,1'-oxybisethane, tetrahydrofuran, 1,4-dioxane and the like; dipolar aprotic solvents, e.g. N,N-dimethylformamide, N,N-dimethylacetamide, acetonitrile, pyridine and the like, or mixtures thereof.

The compounds of formula (I) wherein X is a radical of formula (c), said compounds being represented by formula (I-c), may be prepared by reacting the compounds of formula (I-a) with a phosphorus ylide of formula (VII) (Wittig reaction) or with an ylide of formula (VIII) prepared from a phosphonate (Horner-Emmons reaction).

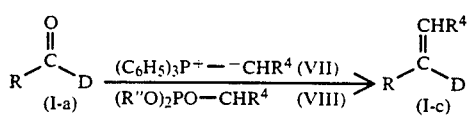

In formula (VIII) R'' represents $C_{1-6}$alkyl. The reaction can conveniently be conducted by treating a phosphonium salt or a phosphonate with an appropriate base such as, for example, butyllithium, methyllithium, sodium amide, sodium hydride, a sodium or potassium alkoxide, sulfinylbis(methane) sodium salt and the like bases, under an inert atmosphere and in a reaction-inert solvent such as for example, a hydrocarbon, e.g. hexane, heptane, cyclohexane and the like; an ether, e.g. 1,1'oxybisethane, tetrahydrofuran, 1,2-dimethoxyethane and the like; a dipolar aprotic solvent, e.g. dimethylsulfoxide, hexamethylphosphor triamide, and the like solvents; and subsequently treating the thus obtained ylides (VII) or (VIII) with the compound of formula (I-a), optionally at a slightly enhanced temperature.

Alternatively the compounds of formula (I-c) may be prepared by reacting a compound of formula (I-a) with an organometallic reagent of formula (IX) wherein M represents a metal group such as, for example, lithium, halomagnesium, copper lithium and the like; and subsequently dehydrating the alcohol of formula (X), for example by treatment with an appropriate acid, e.g. hydrochloric or sulfuric acid in a solvent.

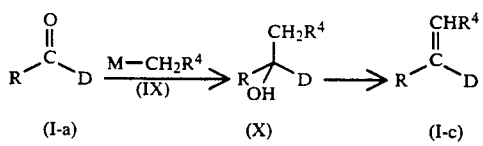

The organometallic reagent may conveniently be prepared following art-known methods by reacting an appropriate halide with a metal such as lithium or magnesium in a reaction-inert solvent such as, for example, an ether, e.g. 1,1'-oxybisethane, tetrahydrofuran, 1,2-dimethoxyethane and the like.

The compounds of formula (I-b) wherein $R^3$ is other than hydrogen, said radical being represented by formula $R^{3-a}$ and said compounds by formula (I-b-1) can also be obtained from compounds of formula (I-b) wherein $R^3$ is hydrogen, said compounds being represented by formula (I-b-2), by O-alkylation or O-silylation with an appropriate alkylating or silylating reagent of formula $R^{3-a}-W^2$.

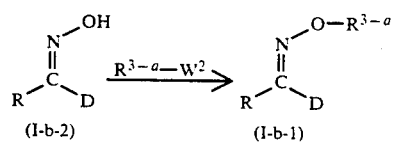

In said alkylating or silylating reagent, $W^2$ represents a leaving group such as, for example, halo, e.g. chloro, bromo, iodo or sulfonyloxy, e.g. 4-methylbenzenesulfonyloxy, benzenesulfonyloxy, 2-naphthalenesulfonyloxy, methanesulfonyloxy, trifluoromethanesulfonyloxy and the like leaving groups. Said O-alkylation and O-silylation reaction can conveniently be conducted by stirring the reactants in a reaction-inert solvent in the presence of a base. Appropriate solvents are halogenated hydrocarbons such as, for example, dichloromethane, trichloromethane and the like; etherts, e.g. 1,1'-oxybisethane, tetrahydrofuran and the like; dipolar aprotic solvents, e.g. N,N-dimethylformamide, N,n-dimethylacetamide, pyridine, acetonitrile; and the like solvents. Suitable bases are tertiairy amines such as, for example, N,N-diethylethanamine, 4-methylmorpholine, pyridine, tetramethylguanidine and the like.

Furthermore, the compounds of formula (I-b-2) which may occur as E-or Z-forms, or mixtures thereof, may be isomerized by equilibration in an acidic medium.

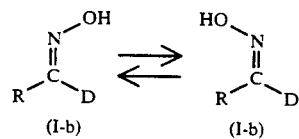

The compounds of formula (I-b-1) wherein $R^{3-a}$ is tri($C_{1-6}$alkyl)silyl can be desilylated to the oximes of formula (I-b) by treatment with a fluoride salt such as, for example, potassium fluoride, tetrabutyl ammonium fluoride, or by reaction with hydrofluoric acid, in a solvent such as, an ether, e.g. 1,1'-oxybisethane, tetrahydrofuran; or in an aqueous mixture thereof. As the compounds of formula (I-b-1) wherein $R^{3-a}$ is tri($C_{1-6}$alkyl)silyl can easily be separated in the E- and Z-stereoisomers following art-known procedures such as selective crystallization and chromatography, and desilylated as described hereinabove, this sequence provides an efficient procedure for preparing those stereomers of (I-b) which can not be prepared by the isomerization procedure mentioned hereinabove.

The compounds of formula (I-b-1) wherein $R^{3-a}$ is $C_{1-6}$alkyl substituted with COOH, COO$C_{1-6}$alkyl, CONR$^5$R$^6$ or COOCH$_2$CONR$^7$R$^8$ and the compounds of formula (I-c) wherein R$^4$ is COOH, COO$C_{1-4}$alkyl, CONR$^5$R$^6$, COOCH$_2$CONR$^7$R$^8$ or $C_{1-6}$alkyl substituted with COOH, COO$C_{1-4}$alkyl, CONR$^5$R$^6$ or COOCH$_2$CONR$^7$R$^8$ can be converted into each other following art known procedures such as, for example, esterification, amidation, transesterification, transamidation, ester hydrolysis and the like methods.

For example, the compounds wherein $R^{3-a}$ or R$^4$ is $C_{1-6}$alkyl substituted with COOH or R$^4$ is COOH may be converted into an ester wherein $R^{3-a}$ or R$^4$ is $C_{1-4}$alkyl substituted with COO$C_{1-4}$alkyl or COOCH$_2$CONR$^7$R$^8$, or R$^4$ is COO$C_{1-4}$alkyl or COOCH$_2$CONR$^7$R$^8$, or into an amide wherein $R^{3-a}$ or R$^4$ is $C_{1-6}$alkyl substituted with CONR$^5$R$^6$ or R$^4$ is CONR$^5$R$^6$ by treating the carboxylic acid with an alkanol of formula C$_{1-4}$alkyl-OH or an alcohol of formula HOCH$_2$CONR$^7$R$^8$ or an amine of formula HNR$^5$R$^6$ in the presence of a suitable reagent capable of forming esters and/or amides. Typical examples of such reagents are for example, dicyclohexylcarbodiimide, 2-chloro1-methylpyridinium iodide, phosphorus pentoxide, 1,1'-carbonylbis[1H-imidazole], 1,1'-sulfonylbis[1H-imidazole] and the like reagents. Alternatively, said carboxylic acids may be converted into suitable reactive functional derivatives thereof such as, for example, an acyl halide, symmetric or mixed anhydride, ester, amide, acyl azide, cyclic anhydride, lactone, lactam and the like derivatives before reaction with the alkanol C$_{1-4}$alkylOH, the alcohol of formula HOCH$_2$CONR$^7$R$^8$ or the amine HNR$^5$R$^6$. Said reactive functional derivatives may be prepared following art known methods, for example, by reacting the carboxylic acid with a halogenating reagent such as, for example, thionyl chloride, phosphorous trichloride, polyphosphorous acid, phosphoryl chloride, oxalyl chloride and the like, or by reacting said carboxylic acid with an acyl halide such as acetyl chloride and the like. Said reactive functional derivatives of the carboxylic acids may be generated in situ, or if desired, be isolated and further purified before reacting them with the alkanol C$_{1-4}$alkyl-OH, the alcohol of formula HOCH$_2$CONR$^7$R$^8$ or the amine HNR$^5$R$^6$.

Said esterification and amidation reactions can conveniently be carried out by stirring the reactants, optionally in a suitable reaction-inert solvent such as, for example, a halogenated hydrocarbon, e.g. dichloromethane, trichloromethane and the like; an aromatic hydrocarbon, e.g. benzene, methylbenzene and the like; an ether, e.g. 1,1'-oxybisethane, tetrahydrofuran and the like; or a dipolar aprotic solvent, e.g. N,N-dimethylformamide, N,N-dimethylacetamide, pyridine and the like. In some instances it may be appropriate to employ an excess of one of the reagents as solvent. The water, acid, alcohol or amine which is liberated during the course of the reaction may be removed from the reaction mixture by art-known procedures such as, for example, azeotropical distillation, complexation, salt formation and the like methods. In some instances particularly the addition of a suitable base such as, for example, an amine, e.g. N,N-diethylethanamine, 4-ethylmorpholine, pyridine or N,N-dimethyl-4-pyridinamine, may be appropriate. Further, in order to enhance the rate of the reaction, said acylation reaction may advantageously be conducted at a somewhat elevated temperature, in particular the reflux temperature of the reaction mixture.

Transesterification may be accomplished by reacting a compound wherein R$^{3-a}$ or R$^4$ is C$_{1-6}$alkyl substituted with COOC$_{1-4}$alkyl or COOCH$_2$CONR$^7$R$^8$ or R$^4$ is COOC$_{1-4}$alkyl or COOCH$_2$CONR$^7$R$^8$, with a different alkanol of formula C$_{1-4}$alkylOH or a different alcohol of formula HOCH$_2$CONR$^7$R$^8$. The equilibrium of the transesterification reaction may be shifted following art-known methods, e.g. by using an excess of said alcohol, or by distilling off the liberated alcohol. Transamination can be accomplished in a similar manner by reaction with an amine HNR$^5$R$^6$.

The compounds wherein R$^{3-a}$ or R$^4$ is C$_{1-6}$alkyl substituted with COOC$_{1-4}$alkyl or COOCH$_2$CONR$^7$R$^8$ or R$^4$ is COOC$_{1-4}$alkyl or COOCH$_2$CONR$^7$R$^8$ can be hydrolysed to the corresponding compounds wherein R$^{3-a}$ or R$^4$ is C$_{1-6}$alkyl substituted with COOH or R$^4$ is COOH. Said hydrolysis can conveniently be conducted by stirring and heating the ester in an aqueous and/or alcoholic medium, e.g. water, methanol, ethanol and the like, or mixtures thereof, in the presence of a base such as, for example, sodium hydroxide, potassium hydroxide, potassium carbonate and the like. In some instances, for example, the 1,1-dimethylethyl ester, said hydrolysis may also be effected by stirring and optionally heating in an acidic aqueous and/or alcoholic medium as defined hereinabove.

Alternatively the compounds of formula (I-b-1) may be prepared from an intermediate of formula (XI) wherein W$^3$ represents a suitable reactive leaving group such as, for example, halo, e.g. chloro, or acetate, by reaction with a reagent of formula (XII).

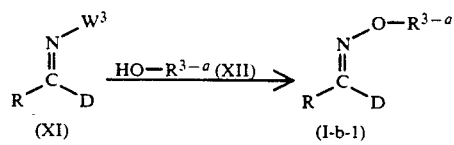

The compounds of formula (I) may also be prepared by cyclizing an intermediate of formula (XIII) or an intermediate of formula (XIV).

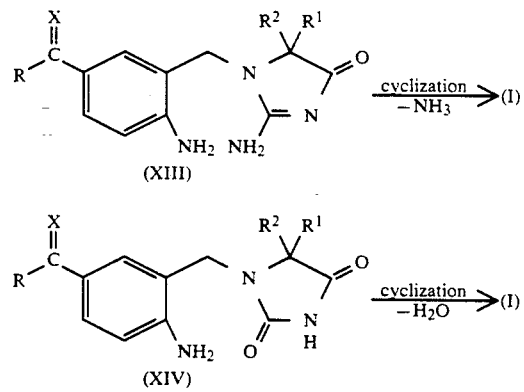

Following an alternative cyclization procedure, an intermediate of formula (XV) may also be converted into a compound of formula (I).

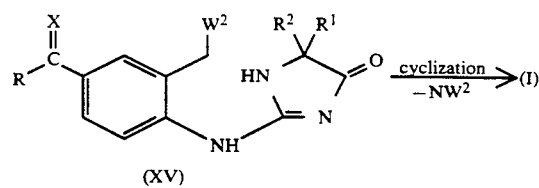

The compounds of formula (I) may also be formed from the quinazoline derivatives (XVI), (XVII) or (XVIII) by cyclization.

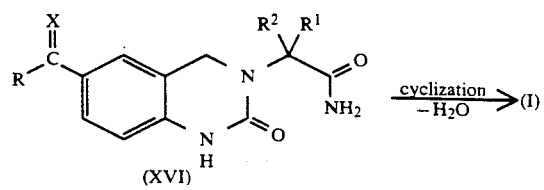

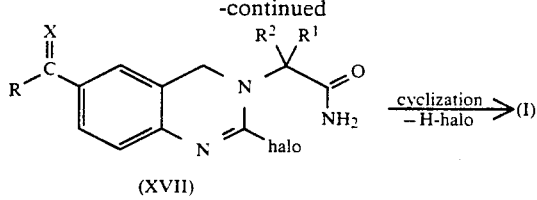

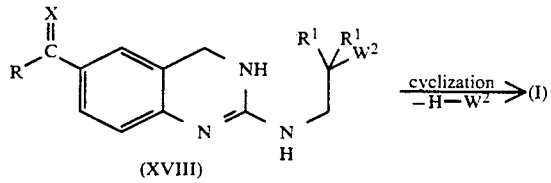

In all the above mentioned cyclization reactions, said cyclization may be carried out by stirring and if desired heating the intermediate starting material, optionally in a suitable reaction-inert solvent. Appropriate solvents for said cyclization reactions are for example, aromatic hydrocarbons, e.g. benzene, methylbenzene, dimethylbenzene and the like; halogenated hydrocarbons, e.g. trichloromethane, tetrachloromethane, chlorobenzene and the like; ethers, e.g. 1,1'-oxybisethane, tetrahydrofuran, 1,4-dioxane, 1,2-dimethoxyethane, methoxybenzene and the like; dipolar aprotic solvents, e.g. N,N-dimethylformamide, N,N-dimethylacetamide, dimethyl sulfoxide and the like; or mixtures of such solvents. The water, hydrohalic acid or ammonia which is liberated during the cyclization reaction may be removed from the reaction mixture by azeotropical destillation, destillation, complexation, salt formation and the like methods.

All intermediates of the previous reaction schemes as well as many of their precursors are novel and have especially been developed for conversion into the compounds of the present invention. Interesting are the novel intermediates of formula (II) and (IV), in particular these intermediates of formula (IV) wherein L is $C_{1-6}$alkyloxy, hydroxy or amino, the pharmaceutically acceptable acid and base addition salts thereof and the stereochemically isomeric forms thereof.

The intermediates of formula (II) can be obtained from the corresponding nitro derivatives of formula (XIX) following art known reduction procedures.

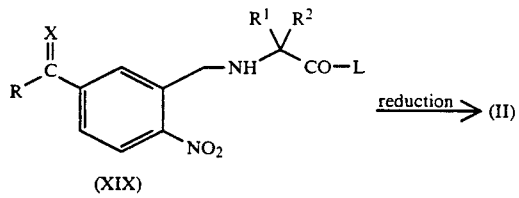

For example, the nitro derivative of formula (XIX) may be reduced by catalytic hydrogenation in a suitable solvent, e.g. methanol or ethanol, in the presence of hydrogen and an appropriate catalyst, e.g. platinum-on-charcoal, palladium-on-charcoal, Raney nickel and the like, optionally at an increased temperature and/or pressure. In some instances it may be useful to add an appropriate catalyst poison such as thiophene to the reaction mixture. Alternatively, said nitro derivative may also be reduced by a reducing agent such as, for example, sodium sulfide, sodium hydrogen sulfide, sodium hydrosulfite, titanium trichloride, formic acid, N,N-diethylethanamine; iron ammonium chloride and the like.

The intermediate nitro derivative (XIX) can be prepared from an intermediate of formula (XX) by reaction with an aminoacid (L=OH) or a derivative thereof (L=—O—$C_{1-6}$alkyl, —O—phenyl, -amino) of formula (XXI) and more particularly an acid addition salt thereof.

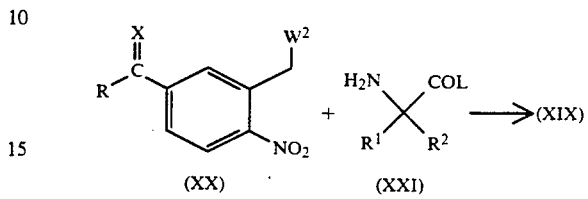

In formula (XX) $W^2$ represents an appropriate leaving group as defined hereinabove. The above N-alkylation reaction can conveniently be conducted by stirring, and if desired heating, the reactants in a suitable reaction-inert solvent in the presence of a base.

Suitable solvents are, for example, water; an aromatic solvent, e.g. benzene, methylbenzene, dimethylbenzene, chlorobenzene, methoxybenzene and the like; a $C_{1-6}$alkanol, e.g. methanol, ethanol, 1-butanol and the like; a ketone, e.g. 2-propanone, 4-methyl-2-pentanone and the like; an ester, e.g. ethylacetate, γ-butyrolactone and the like; an ether, e.g. 1,1'-oxybisethane, tetrahydrofuran, 1,4-dioxane and the like; a dipolar aprotic solvent, e.g. N,N-dimethylformamide, N,N-dimethylacetamide, dimethylsulfoxide, pyridine, 1,3-dimethyl-3,4,5,6-tetrahydro-2(1H)-pyrimidinone, 1,3-dimethyl-2-imidazolidinone, 1,1,3,3-tetramethylurea, 1-methyl-2-pyrrolidinone, nitrobenzene, acetonitrile and the like; or a mixture of such solvents. In order to set free the base form of (XXI) in case a salt form is used, and to neutralize the acid which is formed during the course of the reaction, an appropriate base may be added such as, for example, an alkali metal or an earth alkaline metal carbonate, hydrogen carbonate, hydroxide, oxide, carboxylate, alkoxide, hydride or amide, e.g. sodium carbonate, sodium hydrogen carbonate, potassium carbonate, sodium hydroxide, calcium oxide, sodium acetate, sodium methoxide, sodium hydride, sodium amide and the like, or an organic base such as, for example, an amine, e.g. N,N-diethylethanamine, N-(1-methylethyl)-2-propanamine, 4-ethylmorpholine, 1,4-diazabicyclo[2.2.2]octane, pyridine and the like.

The intermediate of formula (XX) can be obtained from a benzylalcohol of formula (XXII) following art known procedures for converting hydroxy groups into reactive leaving groups.

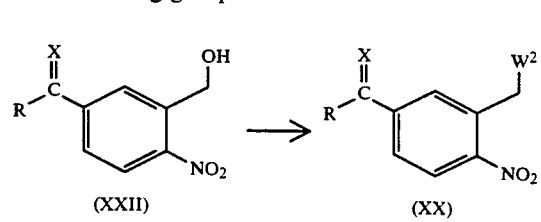

Suitable procedures comprise, for example, converting the alcohol of formula (XXII) into sulfonyloxy esters by reaction with sulfonyl halides such as, for example, methanesulfonyl chloride, benzenesulfonyl chloride, 4-methylbenzenesulfonyl chloride and the like reagents.

Or, the alcohol of formula (XXII) can be converted into the corresponding halide by reaction with a halogenating reagent such as, for example, a hydrohalic acid, e.g. hydrochloric or hydrobromic acid, thionyl chloride, oxalyl chloride, phosphoryl chloride or bromide, phosphorous trichloride or tribromide, phosphorus pentachloride, triphenylphosphine with tetrachloromethane or tetrabromomethane and the like halogenating reagents.

The intermediate benzylalcohol of formula (XXII) can be derived from a protected alcohol by art-known deprotection procedures.

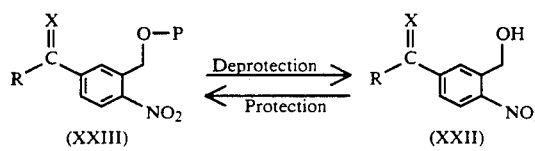

In formula (XXIII) P may represent a suitable protective group such as, for example, tetrahydropyranyl, 2-methoxyethoxymethyl, 2-methoxypropyl, 2-acetoxypropyl, 1-ethoxyethyl and the like; a trialkylsilyl group, e.g. trimethylsilyl, tert.butyldimethylsilyl and the like groups. Said deprotection reaction can easily be conducted following art-known methods of hydrolyzing acetals and silyl ethers, e.g. by acid hydrolysis in aqueous media. Conversely, the protected intermediates of formula (XXIII) may be obtained from the alkanols of formula (XXII) following art-known procedures for protecting hydroxy groups. Typically such protection reactions may comprise treatment with a vinylether, e.g. dihydropyran, in an inert solvent and in the presence of an acid catalyst; or O-alkylation or O-silylation with a suitable alkylating reagent such as, for example, a trialkylsilyl halide, e.g. trimethylsilylchloride, tert-.butyldimethylsilylchloride; and the like protection reactions. The intermediates of formula (XXIII) wherein X is a radical of formula (b) or (c), said intermediates being represented by formulae (XXIII-b) and (XXIII-c), can easily be prepared from an intermediate of formula (XXIII-a) wherein X is O, following the procedures described above for the conversion of the compounds of formula (I-a) into the compounds of formula (I-b) and (I-c).

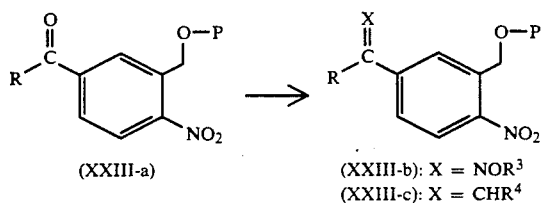

The intermediates of formula (XXIII-a) can be prepared from a cyanide of formula (XXIV) following art-known oxidation procedures such as described in J. Org. Chem., 1975, 40, 267.

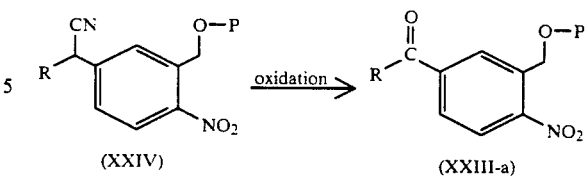

The cyanides of formula (XXIV) can easily be obtained by an aromatic nucleophilic substitution reaction of a cyanide of formula (XXV) on a nitrobenzene of formula (XXVI).

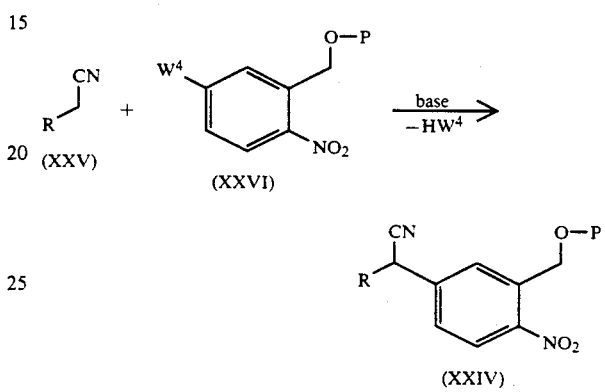

In formula (XXVI) $W^4$ represents a reactive leaving group such as, for example, halo, e.g. chloro or fluoro, nitro, 4-methylbenzenesulfonyloxy, phenyloxy, alkyloxy and the like groups known in the art to be good leaving groups in aromatic nucleophilic substitution reactions. Said aromatic nucleophilic substitution reaction can conveniently be conducted by stirring the reactants in the presence of a base in a reaction inert solvent such as for example, a dipolar aprotic solvent, e.g. N,N-dimethylformamide, N,N-dimethylacetamide, hexamethylphosphoric triamide, pyridine, 1,3-dimethyl-3,4,5,6-tetrahydro-2(1H)-pyrimidinone, 1,3-dimethylimidazolidinone, 1,1,3,3-tetramethylurea, 1-methyl-2-pyrrolidinone, nitrobenzene and the like solvents; or mixtures thereof. Appropriate bases are sodium hydride, sodium amide, sulfinylbis(methane) sodium salt and the like bases. It may be advantageous to add to the reaction mixture a crown ether, e.g. 1,4,7,10,13,16-hexaoxacyclooctadecane and the like or a complexing agent such as for example, tris[2-(2-methoxyethoxy)]ethanamine and the like. Somewhat elevated temperatures may enhance the rate of the reaction.

The intermediates of formula (XXII-a), wherein X is O, can alternatively be prepared by oxidizing an intermediate of formula (XXVII).

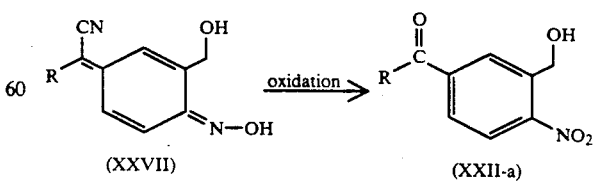

Said oxidation reaction can conveniently be conducted by stirring the reactants in water in the presence of an oxidizing agent such as, for example, hydrogen peroxide and the like.

The intermediates of formula (XXVII) in turn can be obtained by the addition of an intermediate of formula (XXV) to 2-hydroxymethylnitrobenzene.

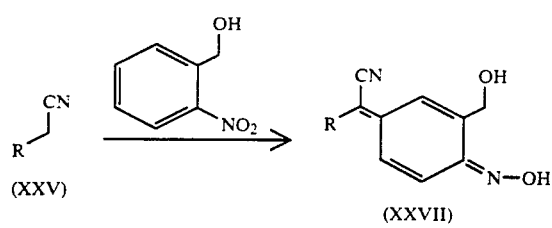

Said addition reaction can conveniently be conducted by stirring the reactants in a reaction-inert solvent in the presence of an appropriate base. Suitable solvents are, for example, dipolar aprotic solvents, e.g. N,N-dimethylformamide, N,N-dimethylacetamide, dimethyl sulfoxide, pyridine and the like. Appropriate bases are sodium hydroxide, potassium hydroxide, sodium hydride, sodium amide, sulfinyl bis(methane) sodium salt and the like bases.

The intermediates of formula (XXII-a) can also be obtained by the chemoselective reduction of an aldehyde of formula (XXVIII).

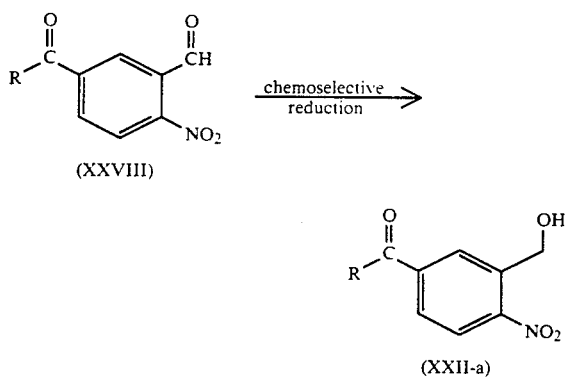

Suitable reductants for said selective reduction of the carboxaldehyde group are, for example, sodium borohydride, sodium cyanoborohydride, and the like. A particularly interesting mode of conducting said reduction comprises the addition of a rare-metal salt such as, for example, cerium(III)chloride, to the reaction in order to increase the selectivity.

The aldehydes of formula (XXVIII) in turn can be obtained by hydrolyzing in an acidic aqueous medium an α-aminocyanide of formula (XXIX), wherein both $R^{10}$ radicals represent an alkyl group such as methyl, ethyl and the like, or both $R^{10}$ taken together form an alkanediyl radical such as, 1,2-ethanediyl, 1,3-propanediyl, 2,2-dimethyl-1,3-propanediyl and the like.

In formula (XXIX) and hereinafter the group -NR'R' represents a dialkylamino group or a heterocyclic radical such as, for example, morpholino, piperidino, pyrrolidino and the like groups.

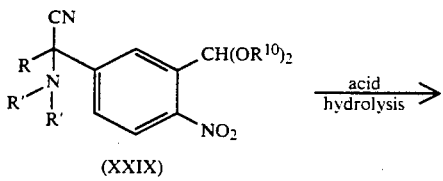

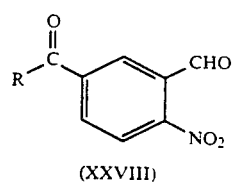

The intermediates of formula (XXIX) in turn can be prepared by an aromatic nucleophilic substitution reaction on a nitrobenzene of formula (XXXI) as described hereinabove for the preparation of the intermediates of formula (XXIV).

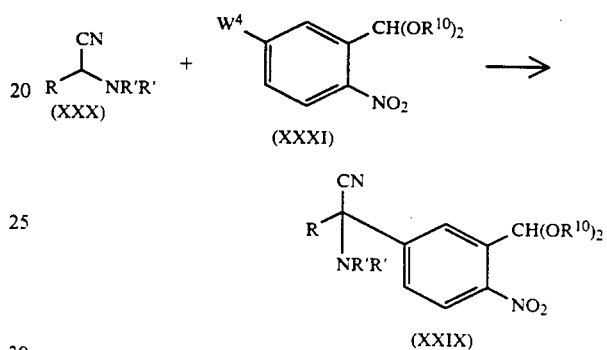

The reagent of formula (XXX) can easily be prepared from an appropriate aldehyde by reaction with sodium cyanide, potassium cyanide and the like cyanides, in the presence of an amine HNR'R' and sodium hydrogen sulfite. Suitable solvents are for example, water, alkanols, e.g. methanol, ethanol and the like, and mixtures thereof.

In a number of instances, the intermediates of formula (XIX) and (II) wherein X is O, said intermediates being represented by formula (XIX-a) and (II-a), can be derived directly from an intermediate of formula (XXVIII) by reductive N-alkylation with an amino acid derivative of formula (XXI) or a salt thereof.

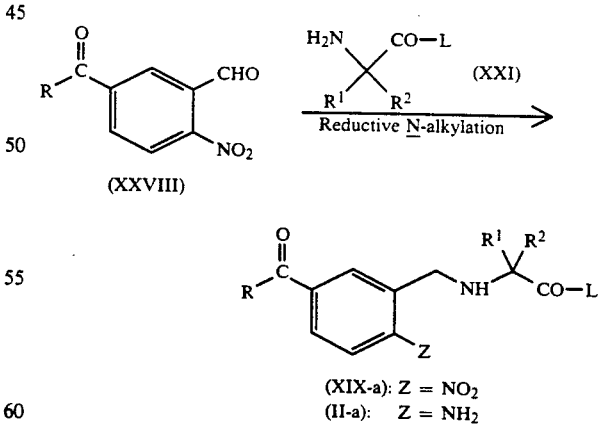

Said reductive N-alkylation reaction can conveniently be conducted following art-known procedures, i.e. by stirring and optionally heating a mixture of the ingredients in a reaction-inert solvent in the presence of a suitable reductant and an equivalent of a base to set free the amino acid from its salt. Suitable bases are alkali metal carboxylates, e.g. sodium acetate, potassium acetate, potassium propionate and the like. For example, said mixture may be catalytically reduced in the presence of hydrogen and a hydrogenation catalyst such as palladium-on-charcoal, platinum-on-charcoal and the like, thus yielding an intermediate of formula (II-a). Alternatively, hydrides, e.g. sodium borohydride, sodium cyanoborohydride and the like; formic acid or a salt thereof, particularly the ammonium salt, may be employed to effect the desired reductive N-alkylation to an intermediate of formula (XIX-a).

The thus obtained intermediates of formula (XIX-a) can further be converted into the corresponding free oxime derivatives wherein X is NOH, said intermediates being represented by formula (XIX-b), by reaction with hydroxylamine or a salt thereof in a lower alkanol such as, for example, methanol, ethanol, 1-propanol, 2-propanol and the like and a suitable base such as, for example, potassium fluoride, potassium acetate and the like.

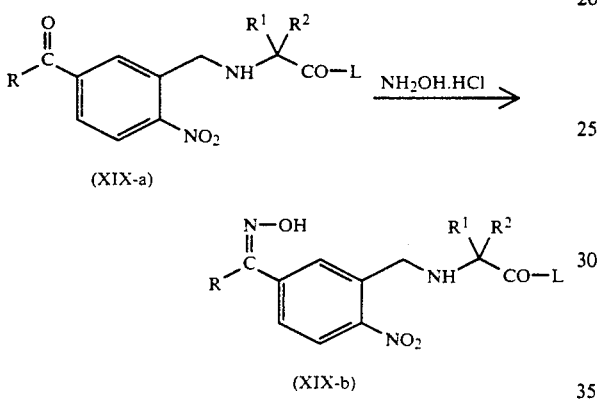

The intermediates of formula (XIX-b) are particularly useful for O-alkylating or O-silylating the oxime group with a reagent of formula $R^{3-a}$-$W^2$ as described hereinbefore for the preparation of compounds of formula (I-b-1) from the compounds of formula (I-b-2). The intermediates of formula (XIX-b) may occur in their E- or Z-form or as mixtures thereof. Mixtures of said E- and Z-forms can be isomerized mainly to the E-form by stirring in a suitable solvent in the presence of an acid such as, for example, hydrochloric acid. Suitable solvents are, for example, alcohols, e.g. propanol, isopropanol and the like; ethers, e.g. 1,4-dioxane, tetrahydrofuran and the like or mixtures of such solvents.

The intermediates of formula (XXII) wherein X is NOH, said intermediates being represented by formula (XXII-b) can also be prepared by reducing an ester of formula (XXXII) wherein $R^{11}$ represents alkyl.

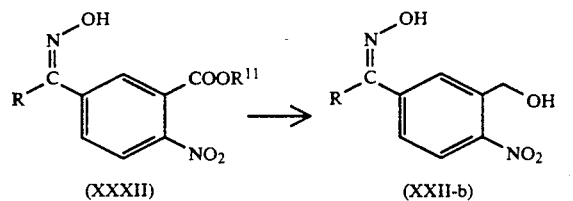

Said reduction can conveniently be conducted by treating the ester in a reaction-inert solvent such as an ether, e.g. tetrahydrofuran, 1,1'-oxybisethane and the like, with a reducing agent such as sodium borohydride.

The intermediates of formula (XXXII) are obtained from the corresponding ketones or aldehydes (XXXIII) following procedures as described hereinabove for the preparation of the compounds of formula (I-b) from those of formula (I-a).

The ketones may be prepared by reacting an organometallic compound $R^{12}$-M, wherein $R^{12}$ represents R but is other than hydrogen, and M is a metal group such as lithium, magnesium halide, copper lithium, with the aldehyde (XXXIII) and oxidizing the thus obtained alcohol to the ketone.

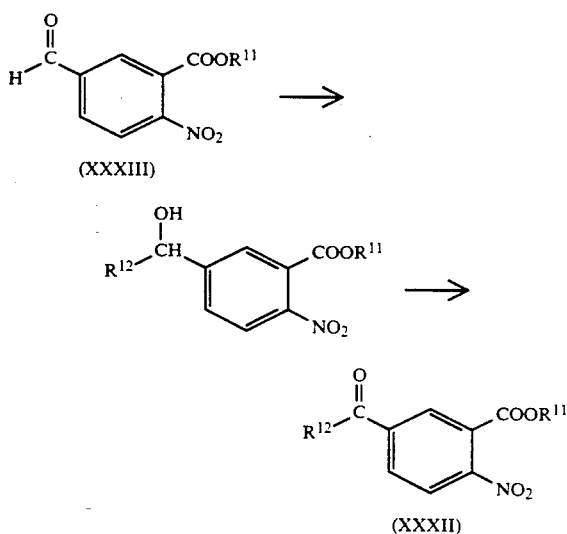

The aldehyde (XXXIII) is prepared following art-known procedures from the corresponding methyl group by oxidation to the carboxylic acid, reduction to the alcohol and oxidation to the aldehyde.

The intermediates of formula (V) wherein X is O, said intermediates being represented by formula (V-a) can be prepared by N-alkylating an intermediate (XXXIV) with an appropriate acetate derivative (XXXV) wherein W and L are reactive leaving groups as defined hereinbefore.

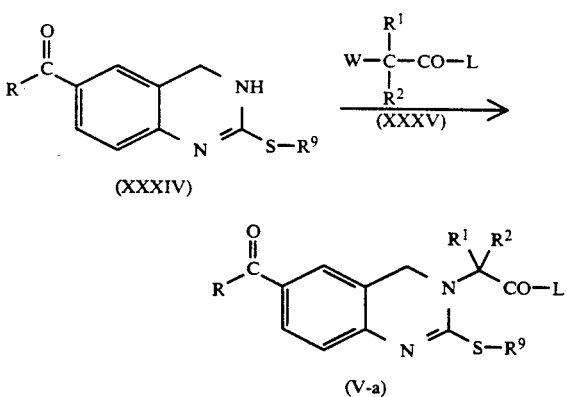

The intermediate (XXXIV) in turn can be obtained from (XXXVI) by S-alkylation with an alkylhalide $R^9$-W, e.g. methyliodide, following art-known procedures.

The intermediate (XXXVI) finally is prepared by the Friedel-Crafts acylation of 3,4-dihydro-2(1H)-quinazolinethione with a suitable acid halide (XXXVII) in the presence of an appropriate Lewis acid such as, for example, aluminum chloride, ferric chloride and the like, in a solvent, preferably a dipolar aprotic solvent, e.g. N,N-dimethylformamide, N,N-dimethylacetamide, hexamethylphosphoric triamide, 1,3-dimethyl-3,4,5,6-tetrahydro-2(1H)-pyrimidinone, 1,3-dimethylimidazolidinone, 1,1,3,3,-tetramethylurea and the like.

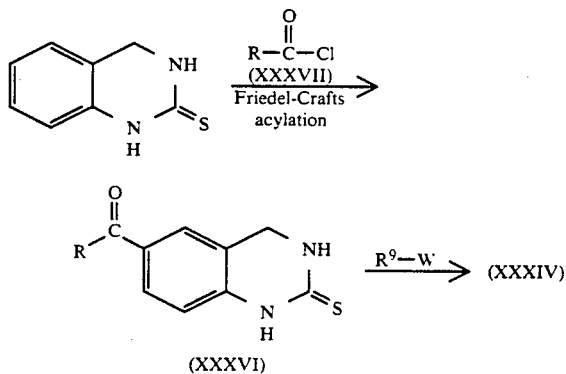

The compounds of formula (I), the pharmaceutically acceptable acid addition salts and stereochemically isomeric forms thereof, are potent inhibitors of the phosphodiesterase type III$_c$ (cardiotonic-sensitive PDE III) (also designated family III$_{A1}$ in the novel classification by J. A. Beavo and D. H. Reifsnyder, TIPS Reviews, April 1990, pp. 150-155) of warm-blooded animals, in particular humans. Inhibition of PDE III$_c$ leads to an elevation of cAMP in cardiac muscle, which in turn enhances sarcolemmal entry of $Ca^{2+}$ into the cell, increases the release and reuptake of $Ca^{2+}$ by the sarcoplasmic reticulum and probably also increases the sensitivity of contractile proteins to $Ca^{2+}$. As a result an increased contractile force of the heart ensures (positive inotropy) as well as a faster relaxation of the heart (positive lusitropy).

Particularly important is the observation that the positive inotropic and lusitropic effects generally do not coincide with a simultaneous increase of other haemodynamic variables such as heart rate and blood pressure. Concommittant increases of heart rate and/or blood pressure would indeed put extra strain on the heart and cancel the beneficial positive cardiac inotropy and lusitropy. In vivo experiments with the instant compounds of formula (I) show moderate systemic vasodilation and hence a decrease in blood pressure. The heart rate generally only increases at high doses. In all, the instant compounds of formula (I) dramatically increase cardiac output by cardiac positive inotropy and lusitropy and without major influence on heart rate and/or blood pressure. The novel intermediates of formula (IV) also are inhibitors of the phosphodiesterase type III$_c$.

Consequently, the subject compounds are considered to be valuable therapeutical drugs for treating warm-blooded animals, particularly humans, suffering from Congestive Heart Failure. Congestive Heart Failure is a pathophysiological state that is defined by the inability of the heart to pump adequate amounts of blood to the peripheral sites of the organism, with consequent failure to meet the metabolic requirement of the body. Said condition may result from a heart attack, infection of the heart, chronic hypertension, deficiencies in the operation of the heart valves and other disorders of the heart leading to Congestive Heart Failure.

In view of their useful positive inotropic and lusitropic properties, the subject compounds may be formulated into various pharmaceutical forms for administration purposes. To prepare the pharmaceutical compositions of this invention, an effective amount of the particular compound, in base or acid addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. Addition salts of the subject compounds are obviously more suitable in the preparation of aqueous compositions due to their increased water solubility.

Especially noteworthy as complexants and/or solubilizers are β-CD, 2,6-dimethyl-β-CD and in particular 2-hydroxypropyl-β-CD, 2-hydroxyethyl-β-CD, 2-hydroxyethyl-γ-CD and 2-hydroxypropyl-γ-CD. In the aforementioned cyclodextrin derivatives, the DS (degree of substitution, i.e. the average number of substituted hydroxy functions per glucose unit) preferably is in the range of 0.125 to 3, in particular 0.3 to 2, more in particular 0.3 to 1 and the MS (molar degree of substitution, i.e. the average number of moles of the substituting agent per glucose unit) is in the range of 0.125 to 10, in particular of 0.3 to 3 and more in particular 0.3 to 1.5, preferably of 0.35 to 0.50. Said compositions may conveniently be prepared by dissolving the cyclodextrin or ether derivative thereof in water and adding thereto a subject compound as well as other adjuvants and components such as, for example, sodium chloride, potassium nitrate, glucose, mannitol, sorbitol, xylitol and buffers such as, for example, phosphate, acetate or citrate buffers; and optionally concentrating or drying the solution by evaporation under reduced pressure or by lyophilization. The amount of the cyclodextrin or ether derivative thereof in the final composition generally ranges from about 1% to about 40% by weight, particularly form 2.5% to 25% and more particularly from 5% to 20%.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions and the like, and segregated multiples thereof.

In view of the usefulness of the subject compounds in the treatment of Congestive Heart Failure it is evident that the present invention provides a method of treating warm-blooded animals suffering from Congestive Heart Failure, said method comprising the systemic administration of a pharmaceutically effective amount of a compound of formula (I), an intermediate of formula (IV) or a pharmaceutically acceptable addition salt thereof in admixture with a pharmaceutical carrier. Those of skill in the treatment of Congestive Heart Failure could easily determine the effective daily amount from the test results presented here. In general it is contemplated that an effective daily amount would be from 0.01 mg/kg to 4 mg/kg body weight, more preferably from 0.04 mg/kg to 2 mg/kg body weight.

It is evident that said effective daily amount may be lowered or increased depending on the response of the treated subject and/or depending on the evaluation of the physician prescribing the compounds of the instant invention. The effective daily amount ranges mentioned hereinabove are therefore guidelines only and are not intended to limit the scope or use of the invention to any extent.

The following examples are intended to illustrate and not to limit the scope of the present invention. Unless otherwise stated all parts therein are by weight.

EXPERIMENTAL PART

A. Preparation of Intermediates

EXAMPLE 1 a) A mixture of 25 parts of 5-chloro-2-nitrobenzenemethanol, 13.3 parts of dihydro-2H-pyran, 300 parts of dichloromethane and 0.28 parts of 4-methylbenzenesulfonic acid was stirred for 2 hours at reflux temperature. After cooling, the reaction mixture was neutralized with sodium carbonate and stirred for 10 min. The whole was filtered and the filtrate was evaporated. The residue was co-evaporated with methylbenzene and then purified by column chromatography (silica gel; CHCl$_3$). The eluent of the desired fraction was evaporated and the residue was co-evaporated with methylbenzene, yielding 36 parts (99.6%) of 2-[(5-chloro-2-nitrophenyl)methoxy]tetrahydro-2H-pyran (interm. 1).

b) To a suspension of 7.13 parts of a sodium hydride dispersion 50% in mineral oil in 94 parts of N,N-dimethylacetamide there was added dropwise a solution of 9.1 parts of benzeneacetonitrile in 18.8 parts of N,N-dimethylacetamide. After hydrogen evolution had ceased, there were added 1.28 parts of N,N-di[2-(2-methoxyethoxy)ethyl]-2-(2-methoxyethoxy)ethanamine and a solution of 20.2 parts of intermediate (1) in 28.2 parts of N,N-dimethylacetamide. After 15 min, the reaction mixture was poured into ice-water and the whole was neutralized. The product was extracted with dichloromethane and the extract was dried, filtered and evaporated, yielding 26.2 parts (100%) of 4-nitro-α-phenyl-3-[[(tetrahydro-2H-pyran-2-yl)oxy]methyl]benzeneacetonitrile (interm. 2).

c) A mixture of 26.2 parts of intermediate (2), 10.2 parts of potassium carbonate and 376 parts of N,N-dimethylacetamide was aerated at room temperature, while stirring. The reaction mixture was poured into water and the product was extracted with 2,2'-oxybispropane. The extract was dried, filtered and evaporated, yielding 25 parts (98.6%) of [4-nitro-3-[[(tetrahydro-2H-pyran-2-yl)oxy]methyl]phenyl] phenyl-methanone (interm. 3).

d) A mixture of 50 parts of intermediate (3), 1.9 parts of 4-methylbenzenesulfonic acid and 400 parts of methanol was stirred at room temperature. The reaction mixture was neutralized with sodium carbonate, stirred at room temperature for 15 min and filtered. The filtrate was evaporated and the residue was stirred in a mixture of water and 2,2'-oxybispropane for 15 min. The whole was washed with NaCl (sat.), dried, filtered and evaporated. The residue was co-evaporated with methylbenzene and was then purified by column chromatography (silica gel; CHCl$_3$/CH$_3$OH 98:2). The eluent of the desired fractions was evaporated and the residue was crystallized from a mixture of methylbenzene and hexane. The product was filtered off, washed with a mixture of hexane and methylbenzene and with hexane, and dried in vacuo at 40°-50° C., yielding 9.7 parts (25.9%) of [3-(hydroxymethyl)-4-nitrophenyl] phenylmethanone; mp. 71.3° C. (interm. 4).

e) to a stirred and cooled (0° C.) mixture of 27.5 parts of intermediate (4), 11.9 parts of N,N-diethylethanamine and 650 parts of dichloromethane there were added dropwise 13.3 parts of methanesulfonyl chloride. The reaction mixture was partitioned between dichloromethane and water. The organic layer was separated, dried, filtered and evaporated, yielding 36 parts (100%) of 5-benzoyl-2-nitrobenzenemethanol methanesulfonate (ester).

To a stirred amount of 385 parts of dimethyl sulfoxide were added 22.3 parts of ethyl glycine monohydrochloride. When a clear solution was obtained, there were added 13.4 parts of sodium hydrogen carbonate and, after stirring for 15 min, 70 parts of molecular sieve 4Å. Stirring was continued for 15 min. Next there were added dropwise a solution of 34.3 parts of 5-benzoyl-2-nitrobenzenemethanol methanesulfonate (ester) in 77 parts of dimethyl sulfoxide. This reaction mixture was used as such for the preparation of intermediate (6). Theoretical yield: 28 parts (100%) of [3-(chloromethyl)-4-nitrophenyl] phenylmethanone (interm. 5).

f) To the reaction mixture, obtained in the preparation of intermediate (5), there were added 9 parts of sodium hydrogen carbonate. The whole was stirred overnight at 50° C. and was then poured into 1000 parts of water. The precipitate was filtered off and stirred in 2-propanone for 15 min. This solution was filtered and the filtrate was evaporated. The residue was taken up in methylbenzene and the whole was washed with water, dried, filtered and evaporated. The residue was purified by column chromatography (silica gel; CHCl$_3$/C$_2$H$_5$OH 98:2). The eluent of the desired fractions was evaporated, yielding 23.7 parts (68.2%) of ethyl N-[(5-benzoyl-2-nitrophenyl)methyl]glycine (interm. 6).

g) A mixture of 3.7 parts of intermediate (6), 2 parts of a solution of thiophene in methanol and 119 parts of ethanol was hydrogenated at normal pressure and at room temperature with 2 parts of platinum-on-charcoal catalyst 5%. After the calculated amount of hydrogen was taken up, the catalyst was filtered off and the filtrate was evaporated. The residue was co-evaporated with methylbenzene, yielding 3.19 parts (95%) of ethyl N-[(2-amino-5-benzoylphenyl)methyl]glycine (interm. 7).

EXAMPLE 2 a) To a stirred solution of 21.2 parts of intermediate (5) in 158 parts of acetonitrile, there were added successively 17.9 parts of ethyl β-alanine monohydrochloride and 20.4 parts of N,N-diethylethanamine. Stirring was continued overnight at 50° C. The reaction mixture was filtered and the filtrate was evaporated. The residue was partitioned between NaCl (sat.) and dichloromethane. The organic layer was separated, dried, filtered and evaporated. The residue was purified by column chromatography (silica gel; CHCl$_3$/C$_2$H$_5$OH 99:1). The eluent of the desired fraction was evaporated and the residue was co-evaporated with methylbenzene, yielding 15.3 parts (55.8%) of ethyl N-[(5-benzoyl-2-nitrophenyl)methyl]-β-alanine (interm. 8).

b) A mixture of 15.3 parts of intermediate (8), 2 parts of a solution of thiophene in methanol 4% and 198 parts of ethanol was hydrogenated at normal pressure and room temperature with 5 parts of palladium-on-charcoal catalyst 5%. After the calculated amount of hydrogen was taken up, the catalyst was filtered off and the filtrate was evaporated. The residue was co-evaporated with methylbenzene, yielding 12.8 parts (93.4%) of ethyl N-[(2-amino-5-benzoylphenyl)methyl]-β-alanine (interm. 9).

In a similar manner there were also prepared: methyl N-[(2-amino-5-benzoylphenyl)methyl]-2-methylalanine (interm. 10) and ethyl 1-[[(2-amino-5-benzoylphenyl)methyl]amino]cyclopropanecarboxylate (interm. 11).

EXAMPLE 3 a) A mixture of 20 parts of intermediate (3), 4.45 parts of hydroxylamine monohydrochloride and 98 parts of pyridine was stirred for a few hours at reflux temperature. The solvent was evaporated and the residue was purified by column chromatography (silica gel; CHCl$_3$/CH$_3$OH 98:2). The eluent of the first and second fraction was evaporated and the residues were separately co-evaporated with ethanol (3×) and with methylbenzene (1×). From the second fraction there were obtained 4.8 parts (30.2%) of product. The first fraction was chromatographed again (silica gel; CHCl$_3$/CH$_3$OH 98:2) and evaporation of the eluent yielded an additional 9 parts (56.4%) of product. Total yield: 13.8 parts (86.6%) of (E+Z)-[3-(hydroxymethyl)-4-nitrophenyl] phenylmethanone, oxime (interm. 12).

b) To a stirred solution of 11.3 parts of intermediate (12) in 245 parts of N,N-dimethylformamide there were added portionwise 1.99 parts of a sodium hydride dispersion 50% in mineral oil. Stirring at room temperature was continued for ½ hour and then there were added at once 6.9 parts of ethyl 2-bromoacetate. After stirring overnight at room temperature, the reaction mixture was poured into NaCl (sat.). The product was extracted with 2,2'-oxybispropane and the extract was washed with water, dried, filtered and evaporated. The residue was purified by column chromatography (silica gel; CHCl$_3$). The eluent of the desired fraction was evaporated and the residue was co-evaporated with methylbenzene, yielding 8.9 parts (59.8%) of ethyl (E+Z)-2-[[[[3-(hydroxymethyl)-4-nitrophenyl]phenylmethylene]amino]oxy]acetate (interm. 13).

c) To a stirred and cooled (0° C.) mixture of 8.9 parts of intermediate (13), 2.6 parts of N,N-diethylethanamine and 260 parts of dichloromethane there were added dropwise 2.84 parts of methanesulfonyl chloride. Stirring was continued at 0° C. and the mixture was allowed to reach room temperature overnight. The product was extracted with 130 parts of dichloromethane and the extract was washed with water (2×), dried, filtered and evaporated. The residue was co-evaporated with methylbenzene, yielding 9.3 parts (100%) of a mixture of ethyl (E+Z)-2-[[[[3-(chloro-methyl)-4-nitrophenyl]phenylmethylene]amino]oxy]acetate (interm. 14) and ethyl (E+Z)-2-[[[[3-[(methylsulfonyloxy)methyl]-4-nitrophenyl]phenylmethylene]amino]oxy]acetate (interm. 15) (15:85).

d) A mixture of 9.3 parts of intermediate (14) and intermediate (15) in 132 parts of dimethyl sulfoxide, 5.15 parts of ethyl glycine monohydrochloride and 7.7 parts of N,N-diethylethanamine was stirred at 50°-60° C. The reaction mixture was poured into NaCl (sat.) and the product was extracted with 2,2'-oxybispropane. The extract was washed with water (2×), dried, filtered and evaporated. The residue was co-evaporated with methylbenzene (2×), yielding 6.6 parts (60%) of ethyl (E+Z)-[[5-[[(2-ethoxy-2-oxoethoxy)imino]phenylmethyl]-2-nitrophenyl]methyl]glycine (interm. 16).

e) A mixture of 6.6 parts of intermediate (16), 4 parts of a solution of thiophene in methanol and 200 parts of ethanol was hydrogenated at normal pressure and at room temperature with 2 parts of platinum-on-charcoal catalyst 5%. After the calculated amount of hydrogen was taken up, the catalyst was filtered off and the filtrate was evaporated. The residue was co-evaporated with methylbenzene, yielding 5.9 parts (96.4%) of ethyl (E+Z)-N-[[2-amino-5-[[(2-ethoxy-2-oxoethoxy)imino]phenylmethyl]phenyl]methyl]glycine (interm. 17).

In a similar manner there were also prepared:
ethyl (E)-N-[[2-amino-5-[[[[6-(cyclohexylmethylamino)-6-oxohexyl]oxy]imino]-phenylmethyl]phenyl]methyl]glycine (interm. 18) and
ethyl (E+Z)-5-[[[[4-amino-3-[[(2-ethoxy-2-oxoethyl)amino]methyl]phenyl]phenylmethylene]amino]oxy]pentanoate (interm. 19).

EXAMPLE 4

To a suspension of 39.3 parts of intermediate (12) in 395 parts of 2-methyl-2-propanol there were added 23 ml of a solution of potassium hydroxide in ethanol and 23.1 parts of ethyl 2-propenoate. The whole was stirred for 3 days at 40° C. The reaction mixture was filtered and the filtrate was evaporated. The residue was purified by column chromatography (silica gel; CH$_2$Cl$_2$/CHOH 98:2). The eluent of the desired fraction was evaporated, yielding 29.9 parts (57.4%) of ethyl (E+Z)-3-[[[[3-(hydroxymethyl)-4-nitrophenyl]phenylmethylene]amino]oxy]propanoate (interm. 20). Following the reaction procedure described in Example 3(c), (d) and (e), intermediate (20) was converted into ethyl (E+Z)-3-[[[[4-amino-3-[[(2-ethoxy-2-oxoethyl- )amino]methyl]phenyl]phenylmethylene]amino]oxy]-propanoate (interm. 21).

EXAMPLE 5 a) To a stirred mixture of 20 parts of intermediate (3) in 98 parts of pyridine, there were added 4.45 parts of hydroxylamine monohydrochloride. The whole was refluxed for a few hours and was then evaporated. The residue was purified by column chromatography (silica gel; CHCl$_3$/CH$_3$OH 98:2). The eluent of the desired fraction was evaporated and the residue was co-evaporated with ethanol (3×) and methylbenzene (1×). The product was chromatographed again (silica gel; CHCl$_3$/CH$_3$OH 100:0→98:2). Evaporation of the eluent yielded 6.4 parts (30.7%) (E+Z)-[4-nitro-3-[[(tetrahydro-2H-pyran-2-yl)oxy]methyl]phenyl]-phenylmethanone, oxime (interm. 22).

b) To a stirred mixture of 6.4 parts of intermediate (22) in 44 parts of dimethyl sulfoxide, there were added 3.29 parts of potassium carbonate and 4.53 parts of 2-chloro-N-cyclohexyl-N-methylacetamide. Stirring was continued overnight at room temperature. The reaction mixture was poured into NaCl (sat.) and the product was extracted with dichloromethane. The extract was dried, filtered and evaporated, yielding 10 parts (100%) of (E+Z)-N-cyclohexyl-N-methyl-2-[[[[4-nitro1-3-[[(tetrahydro-2H-pyran-2-yl)oxy]methyl]phenyl]-phenylmethylene]amino]oxy]acetamide (interm. 23).

c) A solution of 12.55 parts of intermediate (23) in 200 parts of methanol was treated with 0.45 parts of 4-methylbenzenesulfonic acid and stirred at room temperature. The reaction mixture was neutralized with sodium carbonate and stirred for 10 min. The whole was filtered and the filtrate was evaporated. The residue was purified by column chromatography (silica gel; CHCl$_3$/CH$_3$OH 98:2). The eluent of the desired fractions was evaporated and the residue was co-evaporated with ethanol (2×) and with methylbenzene (2×), yielding 8.6 parts (82.2%) of (E+Z)-N-cyclohexyl-2-[[[[3-(hydroxymethyl)-4-nitro-phenyl]phenylmethylene]amino]oxy]-N-methylacetamide (interm. 24). Following the reaction procedure described in Example 3 (c), (d) and (e), intermediate (24) was converted into ethyl (E+Z)-N-[[2-amino-5-[[[2-(cyclohexylmethylamino)-2-oxoethoxy]imino]phenylmethyl]phenyl]-methyl]glycine (interm. 25). In a similar manner there was also prepared ethyl (E+Z)-4-[[[[4-amino-3-[[(2-ethoxy-2-oxoethyl)amino]methyl]phenyl]phenylmethylene]amino]oxy]butanoate (interm. 26).

EXAMPLE 6 a) To a cooled (10° C.) mixture of 12.96 parts of a dispersion of sodium hydride in mineral oil (50%) in 801 parts of tetrahydrofuran there were added 60.5 parts of ethyl (diethoxyphosphinyl)acetate under a nitrogen atmosphere. After stirring for 20 min at 10°-15° C., there was added a solution of 42 parts of intermediate (3) in 45 parts of tetrahydrofuran under nitrogen. Stirring was continued overnight at 60° C. The reaction mixture was poured into ice-water and the product was extracted with dichloromethane. The extract was dried, filtered and evaporated and the residue was co-evaporated with methylbenzene, yielding 55 parts (100%) of ethyl (E+Z)-3-[4-nitro-3-[[(tetrahydro-2H-pyran-2-yl)oxy]methyl]phenyl]-3-phenyl-2-propenoate (interm. 27).

b) A mixture of 50.6 parts of intermediate (27), 2.3 parts of 4-methylbenzenesulfonic acid and 395 parts of methanol was stirred for 20 hours at room temperature. The reaction mixture was neutralized with sodium carbonate and stirred for 5 min. The whole was filtered and the filtrate was evaporated. The residue was dissolved in dichloromethane and this solution was washed with water, dried, filtered and evaporated. The residue was purified by column chromatography (silica gel; CH$_2$Cl$_2$). The eluent of the desired fraction was evaporated, yielding 28 parts (69.5%) of ethyl (E+Z)-3-[3-(hydroxymethyl)-4-nitrophenyl]-3-phenyl-2-propenoate (interm. 28).

c) To a cooled (0°-5° C.) solution of 28 parts of intermediate (28) and 9.7 parts of N,N-diethylethanamine in 665 parts of dichloromethane there were added dropwise 10.4 parts of methanesulfonyl chloride. After stirring for ½ hour at 0°-5° C., the reaction mixture was washed with water, dried, filtered and evaporated. The residue was purified by column chromatography (silica gel; CH$_2$Cl$_2$). The eluent of the desired fraction was evaporated and the residue was co-evaporated with methylbenzene, yielding 27 parts (77.4%) of ethyl (E+Z)-3-[3-[[(methylsulfonyl)oxy]methyl]-4-nitro-phenyl]-3-phenyl-2-propenoate (interm. 29).

d) To a solution of 27 parts of intermediate (29) in 237 parts of acetonitrile, there were added successively 14 parts of ethyl glycine monohydrochloride and 17 parts of N,N-diethylethanamine. The whole was stirred overnight at 50° C. and then evaporated. The residue was taken up in dichloromethane. This solution was washed with water, dried, filtered and evaporated, yielding 26 parts (94.1%) of ethyl (E+Z)-3-[3-[[(2-ethoxy-2-oxoethyl)amino]methyl]-4-nitrophenyl]-3-phenyl-2-propenoate (interm. 30).

e) A mixture of 26 parts of intermediate (30), 18 parts of iron powder, 17.4 parts of ammonium chloride, 596 parts of trichloromethane and 200 parts of water was refluxed for 2 days. The reaction mixture was filtered over diatomaceous earth. The trichloromethane layer of the filtrate was separated, dried, filtered and evaporated. The residue was purified by column chromatography (silica gel; CH$_2$Cl$_2$/CH$_3$OH 99:1). The eluent of the desired fraction was evaporated and the residue was co-evaporated with methylbenzene, yielding 18 parts (72.4%) of ethyl (E+Z)-3-[4-amino-3-[[(2-ethoxy-2-oxoethyl)amino]methyl]phenyl]-3-phenyl-2-propenoate (interm. 31).

f) A mixture of 13.2 parts of intermediate (30) and 119 parts of ethanol was hydrogenated at normal pressure and room temperature with 2 parts of platinum-on-charcoal catalyst 5%. After the calculated amount of hydrogen was taken up, the catalyst was filtered off and the filtrate was evaporated. The residue was purified by column chromatography (silica gel; CHCl$_3$/C$_2$H$_5$OH 98:2). The eluent of the (E)-isomer fraction was evaporated, yielding 4.3 parts (35.1%) of ethyl (E)-3-[4-amino-3-[[(2-ethoxy-2-oxoethyl)-amino]methyl]-phenyl]-3-phenyl-2-propenoate (interm. 32).

g) To a cooled (0°-5° C.) solution of 39.1 parts of intermediate (28), 18.2 parts of N,N-diethylethanamine and 333 parts of dichloromethane there was added dropwise a solution of 16.5 parts of methanesulfonyl chloride in 40 parts of dichloromethane. After stirring for 15 min at 0°-5° C., the reaction mixture was poured into ice-water. The organic layer was separated, dried, filtered and evaporated. The residue was stirred with activated charcoal in 1,1'-oxybisethane. This solution was filtered and concentrated. The crystallized product was filtered off and purified by column chromatography (silica gel; CHCl₃/C₂H₅OH 98:2). The eluent of the desired fraction was evaporated and the residue was crystallized from 1,1'-oxybisethane (2×). The product was filtered off and dried, yielding 16.8 parts (34.5%) of ethyl (Z)-3-[3-[[(methylsulfonyl)oxy]methyl]-4-nitrophenyl]-3-phenyl-2-propenoate; mp. 87.8° C. (interm. 33). Following the reaction procedures described in steps (d) and (f) hereinbefore, intermediate (33) was converted into ethyl (Z)-3-[4-amino-3-[[(2-ethoxy-2-oxoethyl)-amino]methyl]phenyl]-3-phenyl-2-propenoate (interm. 34).

EXAMPLE 7 a) To a stirred amount of 1076 parts of N,N-dimethylacetamide there were added successively 63.24 parts of a dispersion of sodium hydride in mineral oil (50%) and a solution of 92.46 parts of 4-fluorobenzeneacetonitrile in 47 parts of N,N-dimethylacetamide. After hydrogen evolution had ceased, there were added dropwise 9.85 parts of N,N-di[2-(2-methoxyethoxy)ethyl]-2-(2-methoxyethoxy)ethanamine and a solution of 179.19 parts of intermediate (1) in 94 parts of N,N-dimethylacetamide. The mixture was stirred for 15 min. and then partitioned between ice-water and dichloromethane. After neutralization with formic acid, the product was extracted with dichloromethane. The extract was dried, filtered and concentrated, yielding theoretically 244.5 parts (100%) of α-(4-fluorophenyl)-4-nitro-3-[[(tetrahydro-2H-pyran-2-yl)oxy]methyl]benzeneacetonitrile in solution (interm. 35).

b) A mixture of 244.2 parts of intermediate (35), 100.9 parts of sodium carbonate and 1316 parts of N,N-dimethylacetamide was aerated at room temperature for 48 hours, while stirring. The reaction mixture was poured into 3000 parts of water and the whole was extracted with 2,2'-oxybispropane. The formed solid was filtered off, recrystallized from 2-propanol and dried in vacuo, yielding a first fraction of 58.5 parts (24.7%) of product. The organic layer of the filtrate was separated, dried, filtered and evaporated. The residue was stirred in hexane, filtered off and dried, yielding an additional 157 parts (66.2%) of product. Total yield: 215.5 parts (90.9%) of (4-fluorophenyl) [4-nitro-3-[[(tetrahydro-2H-2-pyranyl)oxy]methyl]phenyl]methanone; mp. 105.4° C. (interm. 36). Following the reaction procedures described in Example 1 (d), (e); Example 3 (d) and Example 2 (b), intermediate (36) was converted into ethyl N-[[2-amino-5-(4-fluorobenzoyl)phenyl]methyl]glycine (interm. 37).

Similarly, following the reaction procedures described in Example 1 (d); Example 5 (a), (b); Example 1 (e); Example 2 (a) and Example 1 (g), intermediate (36) was also converted into ethyl (E)-N-[[2-amino-5-[[[2-[(cyclohexyl)methylamino]-2-oxoethoxy]imino](4-fluorophenyl)methyl]phenyl]methyl]glycine (interm. 38). Following the reaction procedures described in Example 1 (d), (e); Example 2(a) and (b), intermediate (36) was converted into ethyl (E+Z)-N-[[2-amino-5-[[[2-[(cyclohexyl)methylamino]-2-oxoethoxy]imino](4-fluorophenyl)methyl]phenyl]methyl]glycine (interm. 39).

EXAMPLE 8 a) To a stirred and cooled (<15° C.) mixture of 134 parts of potassium hydroxide and 940 parts of pyridine were added portionwise 92 parts of 2-nitrobenzenemethanol. Next there were added 132.5 parts of 4-methoxybenzeneacetonitrile and stirring was continued for 4 hours at room temperature. The reaction mixture was diluted with 3000 parts of ice-water and the whole was acidified with 1270 parts of hydrochloric acid. The precipitate was filtered off, stirred overnight in methylbenzene and dried in vacuo at 60° C., yielding 128.8 parts (50.7%) of α-[4-hydroxyimino)-3-(hydroxymethyl)-2,5-cyclohexadien-1-ylidene]-4-methoxybenzeneacetonitrile (interm. 40).

b) To a stirred solution of 340 parts of potassium hydroxide in 1700 parts of water there were added 66.4 parts of intermediate (40). Next a solution of 394 parts of hydrogen peroxide in 500 parts of water was added dropwise. Stirring was continued for 3 hours and then the product was extracted with a mixture of trichloromethane and methanol (90:10). The extract was dried, filtered and evaporated. The residue was purified by column chromatography (silica gel; CHCl₃). The eluent of the desired fractions was collected and the residue was stirred in 2,2'-oxybispropane. The product was filtered off and dried, yielding 21.7 parts (32.8%) of [3-(hydroxymethyl)-4-nitrophenyl](4-methoxyphenyl)-methanone; mp. 116.5° C. (interm. 41).

Following the reaction procedure described in Example 3 (c), (d) and (e), intermediate (41) was converted into ethyl N-[[2-amino-5-(4-methoxybenzoyl)phenyl]methyl]glycine (interm. 42).

EXAMPLE 9 a) A mixture of 14.7 parts of 5-chloro-2-nitrobenzaldehyde, 13.3 parts of trimethoxymethane, 0.15 parts of 4-methylbenzenesulfonic acid and 64 parts of methanol was stirred at reflux temperature. After cooling, the reaction mixture was neutralized with sodium carbonate and stirred for 5 min. The whole was filtered and the filtrate was evaporated, yielding 18.3 parts (99.7%) of 4-chloro-2-(dimethoxymethyl)-1-nitrobenzene (interm. 43).

b) A solution of 78.1 parts of sodium hydrogen sulfite in 400 parts of water was stirred for 15 min at 20° C. under a nitrogen atmosphere. After cooling to −5° C., there were added portionwise 100 parts of 4-bromobenzaldehyde and stirring was continued for 20 min at 10° C. Next there were added portionwise 65.3 parts of morpholine and, after stirring for 15 min, a solution of 26.9 parts of sodium cyanide in 90 parts of water. The mixture was stirred for 22 hours at 50° C. and was then treated with 8.7 parts of a sodium hydroxide solution 50%. The product was filtered off, washed with water and dried in vacuo at 50° C., yielding 138.5 parts (98.5%) of α-(4-bromophenyl)-4-morpholineacetonitrile (interm. 44).

c) To a stirred solution of 21.1 parts of a sodium hydride dispersion 50% in mineral oil in 940 parts of N,N-dimethylformamide there was added dropwise a solution of 112.5 parts of intermediate (44) in 207 parts of N,N-dimethylformamide under a nitrogen atmosphere. After stirring for 2 hours and subsequent cooling to 0°-5° C., there was added dropwise a solution of 94.9 parts of intermediate (43) in 263 parts of N,N-dimethylformamide. Stirring was continued for 45 min at room temperature. The reaction mixture was poured into ice-water. The precipitate was filtered off and dissolved in 2,2'-oxybispropane. This solution was washed with water, dried and filtered. The filtrate was left to crystallize, yielding two crops of respectively 60.2 parts and 36.3 parts of product. Addition of dichloromethane to the mother liquor yielded a third crop of 77.7 parts of product. Total yield: 174.2 parts (91.4%) of α-(4-bromophenyl)-α-[3-(dimethoxymethyl)-4-nitrophenyl]-4-morpholineacetonitrile; mp. 142.8° C. (interm. 45).

d) To a stirred mixture of 390 parts of 2-propanol, saturated with hydrochloric acid and 350 parts of water there was added dropwise a solution of 172.4 parts of intermediate (45) in 361 parts of 1,4-dioxane. After refluxing for 3 hours and stirring at room temperature overnight, the precipitate was filtered off (*) and taken up in a mixture of methanol and dichloromethane. The whole was basified with NH₄OH (aq.), washed with water, dried, filtered and evaporated, yielding a first fraction of 83 parts (62.2%) of product. The filtrate (*) was evaporated. The residue was taken up in water and the whole was extracted with dichloromethane. The extract was washed with water, dried, filtered, evaporated. The residue was co-evaporated with methylbenzene and stirred in 2,2'-oxybispropane. The product was filtered off and dried in vacuo at 40° C., yielding an additional 4.5 parts (3.4%) of product. Total yield: 87.5 parts (65.6%) of 5-(4-bromobenzoyl)-2-nitro-benzaldehyde; mp. 150.9° C. (interm. 46).

e) To a stirred and cooled (ice-bath) solution of 83 parts of intermediate (46), 11.2 parts of cerium(III)chloride heptahydrate and 1540 parts of dimethyl sulfoxide there were added portionwise 2.5 parts of sodium tetrahydroborate. After stirring for 10 min, there was added an ammonium chloride solution. The product was successively extracted with 2,2'-oxybispropane (3×) and with dichloromethane (2×). The combined extracts were washed with water, dried, filtered and evaporated. The residue was purified twice by column chromatography (silica gel; $CH_2Cl_2/CH_3OH$ 99.5:0.5). The eluent of the desired fraction was evaporated, yielding 56.4 parts (67.1%) of (4-bromophenyl)[3-(hydroxymethyl)-4-nitrophenyl]methanone (interm. 47). Following the reaction procedure described in Example 3 (c), (d) and (e), intermediate (47) was converted into ethyl N-[[2-amino-5-(4-bromobenzoyl)phenyl]methyl]glycine (interm. 48).

In a similar manner there were also prepared:
ethyl N-[[2-amino-5-(3-methoxybenzoyl)phenyl]methyl]glycine (interm. 49),
ethyl N-[[2-amino-5-(4-methylbenzoyl)phenyl]methyl]glycine (interm. 50),
ethyl N-[[2-amino-5-(3,4-dimethoxybenzoyl)phenyl]methyl]glycine (interm. 51),
ethyl [[2-amino-5-(4-chlorobenzoyl)phenyl]methyl]glycine (interm. 52).

Following the reaction procedures described in Examples 5 (a), (b); Example 3 (c), (d) and (e), intermediate (47) was also converted into ethyl (E+Z)-N-[[2-amino-5-[(4-bromophenyl)[[2-(cyclohexylmethylamino)-2-oxoethoxy]imino]methyl]phenyl]methyl]glycine (interm. 53).

EXAMPLE 10 a) 106 Parts of N,N-dimethylformamide were added dropwise to 650 parts of aluminum chloride and the solution was stirred for 15 min at 75° C. There were added portionwise 112 parts of 3,4-dihydro-2(1H)-quinazolinethione and, after stirring for 15 min at 75° C., 136 parts of 3-pyridinylcarbonyl chloride hydrochloride. Stirring at 75° C. was continued overnight and then the mixture was poured into 2500 parts of ice-water. The precipitate was filtered off and stirred for 13 hours in a mixture of ice-water and 1530 parts of a sodium hydroxide solution 50%. The product was filtered off, washed with water and dried, yielding 150 parts (82%) of (3-pyridinyl) (1,2,3,4-tetrahydro-2-thioxo-6-quinazolinyl)methanone; (decomp.) (interm. 54).

b) A mixture of 2.7 parts of intermediate (54), 89 parts of tetrahydrofuran, 18.8 parts of N,N-dimethylformamide and 1.45 parts of iodomethane was stirred for 18 hours at room temperature. The reaction mixture was filtered and the filtrate was neutralized with ammonium hydroxide. The product was extracted with dichloromethane. The extract was dried, filtered and evaporated. The residue was purified by column chromatography (silica gel; $CH_2Cl_2/CH_3OH(NH_3)$ 95:5). The eluent of the desired fraction was evaporated and the residue was crystallized from 2,2'-oxybispropane. The product was filtered off and dried, yielding 1.75 parts (61.8%) of [3,4-dihydro-2-(methylthio)-6-quinazolinyl](3-pyridinyl)methanone; mp. 155.8° C. (interm. 55).

c) To a solution of 8.5 parts of intermediate (55) in 47 parts of N,N-dimethylformamide there were added 1.4 parts of a dispersion of sodium hydride in mineral oil (50%). After stirring for 20 min at room temperature, there was added dropwise a solution of 6.12 parts of methyl 2-bromoacetate in 9.4 parts of N,N-dimethylformamide. Stirring at room temperature was continued for ½ hour. The reaction mixture was diluted with water and the product was extracted with methylbenzene. The organic layer was in its turn extracted with diluted hydrochloric acid. The aqueous layer was basified with sodium hydroxide and extracted with methylbenzene. The extract was dried, filtered and evaporated and the residue was purified by column chromatography (silica gel; $CH_3C_6H_5/CH_3CN$ 75:25). The eluent of the desired fraction was evaporated and the residue was crystallized from 1,1'-oxybisethane. The product was filtered off and dried, yielding 1.9 parts (13.3%) of methyl 3.4-dihydro-2-(methylthio)-6-(3-pyridinylcarbonyl)-3-quinazolineacetate; mp. 113.6° C. (interm. 56).

EXAMPLE 11 a) A mixture of 26.7 parts of ethyl N-[[5-(4-methylbenzoyl)-2-nitrophenyl]methyl]glycine (which is a precursor to intermediate 50 in Example 9), 6.25 parts of hydroxylamine monohydrochloride, 5.25 parts of potassium fluoride and 395 parts of ethanol was stirred for 22 hours at reflux temperature. The reaction mixture was evaporated and the residue was dissolved in ethyl acetate. The whole was washed with sodium hydrogen carbonate solution 10% and with water. The organic layer was dried, filtered and evaporated and the residue was purified by column chromatography (silica gel; $CH_2Cl_2/CH_3OH$ 98:2). The eluent of the E- and Z-isomer fractions was evaporated and the residue was crystallized from 2,2'-oxybispropane, yielding 3.7 parts of product. The mother liquor was evaporated and the residue was isomerized in a mixture of 1,4-dioxane and 2-propanol, saturated with HCl, by stirring overnight. The solvent was evaporated and the residue was stirred in water. After neutralizing with NaHCO₃ 10%, the product was extracted with dichloromethane. The extract was dried, filtered and evaporated and the residue was crystallized from 2,2'-oxybispropane, yielding 2 additional fractions of resp. 3.6 parts and 1.2 parts of product. The three fractions were recrystallized from a mixture of ethyl acetate and 2,2'-oxybispropane, yielding 5.3 parts (19%) of ethyl (E)-N-[[5-[(hydroxyimino)(4-methylphenyl)methyl]-2-nitrophenyl]methyl]glycine (interm. 57).

b) To a stirred mixture of 5.3 parts of intermediate (57) in 89 parts of tetrahydrofuran there were added 1.8 parts of 2-methyl-2-propanol, potassium salt and, after 5 min, 0.44 parts of N,N-di[2-(2-methoxyethoxy)ethyl]-2-(2-methoxyethoxy)ethanamine. Next there was added dropwise a solution of 3 parts of 2-chloro-N-cyclohexyl-N-methyl-acetamide in 44.5 parts of tetrahydrofuran. Stirring was continued for 3 hours at room temperature. The reaction mixture was evaporated and the residue was taken up in water. The product was extracted with a mixture of dichloromethane and methanol (90:10). The extract was dried, filtered and evaporated. The residue was purified by column chromatography (silica gel; CH$_3$COOC$_2$H$_5$/hexane 50:50). The eluent of the desired fraction was evaporated, yielding 5.7 parts (77.6%) of ethyl (E)-N-[[5-[[[2-(cyclohexylmethylamino)-2-oxoethoxy]imino](4-methylphenyl)methyl]-2-nitrophenyl]methyl]glycine (interm 58).

c) A mixture of 5.7 parts of intermediate (58), 2 parts of a solution of thiophene in methanol 4% and 119 parts of ethanol was hydrogenated at normal pressure and room temperature with 3 parts of platinum-on-charcoal catalyst 5%. After the calculated amount of hydrogen was taken up, the catalyst was filtered off and the filtrate was evaporated, yielding 5.1 parts (94.6%) of ethyl (E)-N-[[2-amino-5-[[[2-(cyclohexylmethylamino)-2-oxoethoxy]imino](4-methylphenyl)methyl]phenyl]methyl]glycine (interm. 59).

EXAMPLE 12 a) To a stirred and cooled (0° C.: 2-propanone/dry ice) solution of 54.4 parts of methyl 5-methyl-2-nitrobenzoate in 405 parts of acetic anhydride and 394 parts of acetic acid were added dropwise 110 parts of sulfuric acid and portionwise 83.6 parts of chromium(VI)oxide. Stirring was continued for ½ hour at 0°–10° C. and overnight at room temperature. The reaction mixture was poured into ice-water and the whole was treated with dichloromethane. The precipitate which formed, was filtered off, washed with 2,2'-oxybispropane and dried in vacuo at 80° C., yielding 30.2 parts (48.1%) of product. The dichloromethane layer was separated and extracted with a sodium hydrogen carbonate solution and the aqueous extract was acidified with HCl 2N. The precipitate was filtered off and treated similarly as before, yielding an additional 5 parts (8.0%) of product. Total yield: 35.2 parts (56.1%) of 2-nitro-1,5-benzenedicarboxylic acid, 1-methyl ester; mp. 197.5° C. (interm. 60).

From the dichloromethane layer there was also obtained methyl 5-[bis(acetyloxy)methyl]-2-nitrobenzoate; mp. 102.3° C. (interm. 61).

b) To a cooled (−18° C.; 2-propanone/dry ice) solution of 5.63 parts of intermediate (60) in 44.5 parts of tetrahydrofuran there were added dropwise 10.7 parts of a solution of dimethylsulfide borane complex in tetrahydrofuran 2M. The mixture was allowed to warm to room temperature and was then refluxed for 2 hours. There were added 23.7 parts of methanol and refluxing was continued for 10 min. The reaction mixture was evaporated and the residue was taken up in 2,2'-oxybispropane. This solution was successively washed with water, Na$_2$CO$_3$ 5% and water and was then dried, filtered and evaporated. The residual syrup was left overnight to crystallize. The product was recrystallized from 2,2'-oxybispropane, filtered off, washed with 2,2'-oxybispropane and dried in vacuo at room temperature, yielding 2.1 parts (39.8%) of product. Evaporation of the mother liquor yielded an additional 1.9 parts (36.0%) of product. Total yield: 4.0 parts (75.8%) of methyl 5-(hydroxymethyl)-2-nitrobenzoate; mp. 54.5° C. (interm. 62).

c) A mixture of 1.9 parts of intermediate (62), 7.8 parts of manganese(IV)oxide and 133 parts of dichloromethane was stirred over weekend at room temperature. The reaction mixture was filtered over diatomaceous earth. To the filtrate there was added methylbenzene and the whole was filtered again. The filtrate was evaporated, yielding 1.42 parts (75.4%) of methyl 5-formyl-2-nitrobenzoate; mp. 76.7° C. (interm. 63). Hydrolysis of intermediate (61) in an aqueous acidic medium also yielded methyl 5-formyl-2-nitrobenzoate (interm. 63).

d) A mixture of 22 parts of intermediate (63), 8.4 parts of hydroxylamine monohydrochloride and 147 parts of pyridine was heated at 80° C. for 2 hours. The solvent was evaporated and the residual oil was partitioned between water and 2,2'-oxybispropane. The organic layer was separated, washed successively with water, HCl 1N, water, NaHCO$_3$ 5% and water, and was then dried, filtered and evaporated. The residue was dried in vacuo at 60° C., yielding 19.8 parts (80.3%) of methyl (E)-5-[(hydroxyimino)methyl]-2-nitrobenzoate; mp. 116.0° C. (interm. 64).

e) To a refluxing mixture of 18.3 parts of intermediate (64), 12.37 parts of sodium tetrahydroborate and 320 parts of tetrahydrofuran there were added dropwise 56.9 parts of methanol. After refluxing for 1 hour, the reaction mixture was poured into ice-water. The whole was acidified with hydrochloric acid 2N and then extracted with dichloromethane. The extract was washed successively with water, NaHCO$_3$ 5% and water, and was then dried, filtered and evaporated. The residue was purified by column chromatography (silica gel; CH$_2$Cl$_2$/CH$_3$OH/THF 90:5:5). The eluent of the desired fraction was evaporated and the residue was washed with 2,2'-oxybispropane and dried in vacuo at 60° C., yielding 12.6 parts (78.6%) of (E)-3-(hydroxymethyl)-4-nitro-benzaldehyde, oxime; mp. 128.9° C. (interm. 65).

EXAMPLE 13 a) To a stirred mixture of 58.9 parts of potassium acetate, 100.5 parts of ethyl glycine monohydrochloride and 790 parts of ethanol, there were added 100 parts of 5-(3-bromobenzoyl)-2-nitrobenzaldehyde (prepared following the procedure described in Example 9 or Example 14. After stirring for ½ hour, there were added portionwise 9.4 parts of sodium cyanotrihydroborate. Stirring was continued for ½ hour at room temperature. The reaction mixture was evaporated and the residue was partitioned between water and dichloromethane. The organic layer was separated, washed with water, dried, filtered and evaporated. The residue was purified by column chromatography (silica gel; CH$_2$Cl$_2$/C$_2$H$_5$OH 99:1). The eluent of the desired fraction was evaporated, yielding 71 parts (56.2%) of ethyl N-[[5-(3-bromobenzoyl)-2-nitrophenyl]methyl]glycine (interm. 66).

b) A mixture of 68 parts of intermediate (66), 14 parts of hydroxylamine monohydrochloride, 11.6 parts of potassium fluoride and 790 parts of ethanol was stirred for 3 hours at reflux temperature. After cooling, the reaction mixture was filtered. The precipitate was rinsed with ethanol and the combined filtrates were evaporated. The residue was taken up in a mixture of ethyl acetate and water and the whole was neutralized with NaHCO$_3$ 10%. The organic layer was separated, washed with water, dried, filtered and evaporated, yielding 51.4 parts of product (E/Z isomer mixture) (1). From the aqueous layer, a precipitate was filtered off, which was washed with 2,2′-oxybispropane and dried in vacuo at 60° C., yielding an additional 8.7 parts of product (mainly Z-isomer) (2). Total yield: 60.1 parts (86.1%) of (E/Z) isomer mixture, which can be separated by column chromatography. A fraction of (1) was crystallized from 2-propanone to obtain a small amount of pure ethyl (E)-N-[[5-[(3-bromophenyl) (hydroxyimino)methyl]-2-nitrophenyl]methyl]glycine; mp. 131.2° C. (interm. 68). Crystallization of (2) from ethyl acetate yielded a small amount of pure ethyl (Z)-N-[[5-[(3-bromophenyl) (hydroxyimino)methyl]-2-nitrophenyl]methyl]glycine; mp. 149.8° C. (interm. 67).

c) To a stirred solution of 5.3 parts of intermediate (68) in 89 parts of tetrahydrofuran there were added 1.46 parts of 2-methyl-2-propanol, potassium salt and, after 5 min, 0.38 parts of 2-(methoxyethoxy)-N,N-bis[2-(methoxyethoxy)ethyl]ethanamine and a solution of 2.46 parts of chloro-N-cyclohexyl-N-methylacetamide in some tetrahydrofuran. Stirring was continued for 20 min. The reaction mixture was evaporated and the residue was stirred in water. The product was extracted with a mixture of ethanol and dichloromethane (10:90). The extract was dried, filtered and evaporated and the residue was purified by column chromatography (silica gel; hexane/CH$_3$COOC$_2$H$_5$ 50:50). The eluent of the desired fraction was evaporated and the residue was co-evaporated with methylbenzene, yielding 5 parts (70.7%) of ethyl (E)-N-[[5-[(3-bromophenyl)[[2-(cyclohexylmethylamino)-2-oxoethoxy]imino]methyl]-2-nitrophenyl]methyl]glycine (interm. 69).

d) A mixture of 5 parts of intermediate (69), 2 parts of a solution of thiophene in methanol 4% and 158 parts of ethanol was hydrogenated overnight at normal pressure and room temperature with 2 parts of palladium-on-charcoal catalyst 10%. After the calculated amount of hydrogen was taken up, the catalyst was filtered off and the filtrate was evaporated. The residue was co-evaporated with methylbenzene, yielding 4.6 parts (96.7%) of ethyl (E)-N-[[2-amino-5-[(3-bromophenyl)[[2-(cyclohexylmethylamino)-2-oxoethoxy]imino]methyl]phenyl]methyl]glycine (intermediate 70). In a similar manner there were also prepared:

ethyl (Z)-N-[[2-amino-5-[[[(3-bromophenyl)-2-(cyclohexylmethylamino)-2-oxoethoxy]imino]methyl]phenyl]methyl]glycine (interm. 71);

ethyl (E)-N-[[2-amino-5-[[[2-(cyclohexylmethylamino)-2-oxoethoxy]imino][4-(trifluoromethyl)phenyl]methyl]phenyl]methyl]glycine (interm. 72);

ethyl (E+Z)-N-[[2-amino-5-[[[2-(cyclohexylmethylamino)-2-oxoethoxy]imino](3-methylphenyl)methyl]phenyl]methyl]glycine (interm. 73);

ethyl (Z)-N-[[2-amino-5-[[[2-(cyclohexylmethylamino)-2-oxoethoxy]imino](3-methylphenyl)methyl]phenyl]methyl]glycine (interm. 74);

ethyl (Z)-N-[[2-amino-5-[[[2-(cyclohexylmethylamino)-2-oxoethoxy]imino][4-(trifluoromethyl)phenyl]methyl]phenyl]methyl]glycine (interm. 75);

ethyl (Z)-N-[[2-amino-5-[(3-chlorophenyl)[[2-(cyclohexylmethylamino)-2-oxoethoxy]imino]methyl]phenyl]methyl]glycine (interm. 76);

ethyl (E)-N-[[2-amino-5-[(3-chlorophenyl)[[2-(cyclohexylmethylamino)-2-oxoethoxy]imino]methyl]phenyl]methyl]glycine (interm. 77);

ethyl (E)-N-[[2-amino-5-[[[2-(cyclohexylmethylamino)-2-oxoethoxy]imino](3-methoxyphenyl)methyl]phenyl]methyl]glycine (interm. 78); and ethyl (Z)-N-[[2-amino-5-[[[2-(cyclohexylmethylamino)-2-oxoethoxy]imino](2-thienyl)methyl]phenyl]methyl]glycine (interm. 79).

EXAMPLE 14 a) 81.6 Parts of a dispersion of sodium hydride in mineral oil (50%) were stirred in hexane to remove the oil. The solvent was decanted and to the residue there were added 825 parts of dimethyl sulfoxide. While stirring at room temperature, there were added dropwise a solution of 92.3 parts of 2-thiopheneacetonitrile in 138 parts of dimethyl sulfoxide (when necessary, cooling on ice) and next a solution of 173.7 parts of intermediate (43) in 138 parts of dimethyl sulfoxide. Stirring at room temperature was continued overnight. The crude reaction mixture was used as such for further synthesis. Yield: 238.8 parts (100%) of α-[3-(dimethoxymethyl)-4-nitrophenyl]-2-thiopheneacetonitrile (interm. 80).

b) A mixture of 238.8 parts of intermediate (80), 40.8 parts of a dispersion of sodium hydride in mineral oil (50%) and 1100 parts of dimethyl sulfoxide was stirred at room temperature, while air was bubbled through for a week and oxygen for 40 hours. The reaction mixture was poured into ice-water and the product was extracted with dichloromethane. The extract was dried, filtered and evaporated. The residue was stirred in water and the whole was re-extracted with dichloromethane. The extract was dried, filtered and evaporated and the residue was purified by column chromatography (silica gel; CH$_2$Cl$_2$). The eluent of the desired fraction was evaporated, yielding 181.5 parts (78.7%) of [3-(dimethoxymethyl)-4-nitrophenyl](2-thienyl)methanone (interm. 81).

c) A mixture of 181.5 parts of intermediate (81), 468 parts of 2-propanol saturated with hydrochloric acid, 371 parts of 1,4-dioxane and 240 parts of water was stirred for 18 hours at reflux temperature. After cooling, the precipitate was filtered off, washed with 2-propanol and 2,2′-oxybispropane and dried, yielding 89.7 parts (58.2%) of product. The filtrate was concentrated to obtain further precipitation. The precipitate was filtered off, washed successively with 2-propanol, diluted NH$_4$OH, water, 2-propanol and 2,2′-oxybispropane, and dried, yielding an additional 25.4 parts (16.5%) of product. Total yield: 115.1 parts (74.7%) of 2-nitro-5-(2-thienylcarbonyl)benzaldehyde (interm. 82).

In a similar manner there was also prepared 2-nitro-5-[4-(trifluoromethyl)benzoyl]benzaldehyde; mp. 119.5° C. (interm. 83)

B. Preparation of the final compounds

EXAMPLE 15

To a stirred and cooled (0°-5° C.) solution of 3.19 parts of intermediate (7) in 40 parts of ethanol there was added dropwise a solution of 1.13 parts of bromocyanide in 8 parts of ethanol. Stirring was continued overnight at room temperature and for 3 hours at reflux temperature. After cooling, the reaction mixture was treated with methanol, saturated with ammonia. The precipitate was filtered off, washed with ethanol, stirred in water and boiled in ethanol. The impure product was filtered off, washed with ethanol and 2,2′-oxybispropane and recrystallized from a mixture of 16 parts of methanol and 75 parts of N,N-dimethylformamide. The product was filtered off, washed with methanol and 2,2'-oxybispropane and dried in vacuo at 70°-75° C., yielding 1.08 parts (36.3%) of 7-benzoyl-3,5-dihydroimidazo[2,1-b]quinazolin-2(1H)-one; mp.>300° C. (comp. 1).

EXAMPLE 16

To a stirred and cooled (0° C.) solution of 9.5 parts of intermediate (25) in 160 parts of ethanol there was added dropwise a solution of 2.08 parts of bromocyanide in ethanol. Stirring was continued for 1 ½ hour at 0° C., for 1 hour at room temperature and for 2 hours at reflux temperature. The reaction mixture was evaporated and the residue was partitioned between NaCl (sat.) and dichloromethane. After neutralization with a sodium hydroxide solution, the product was extracted with dichloromethane. The extract was dried, filtered and evaporated. The residue was purified twice by column chromatography (silica gel; CHCl$_3$/CH$_3$OH/CH$_3$OH(NH$_3$) 98:1:1; HPLC; silica gel; CHCl$_3$/CH$_3$OH 93:7). The first and second fraction were separately evaporated and the residues were crystallized from ethyl acetate. The products obtained from both fractions were filtered off, washed with ethyl acetate and 2,2'-oxybispropane and dried in vacuo at 60° C., yielding resp. 2.92 parts (32.2%) of (Z)-N-cyclohexyl-N-methyl-2-[[[phenyl(1,2,3,5-tetrahydro-2-oxoimidazo[2,1-b]quinazolin-7-yl)methylene]amino]oxy]acetamide; mp. 173.4° C. (comp. 10) and 2.4 parts (26.3%) of (E)-N-cyclohexyl-N-methyl-2-[[[phenyl(1,2,3,5-tetrahydro-2-oxoimidazo[2,1-b]quinazolin-7-yl)methylene]amino]oxy]acetamide; mp. 202.2° C. (comp. 9).

EXAMPLE 17

To a stirred suspension of 16 parts of compound (1) in 440 parts of pyridine there were added 4.17 parts of hydroxylamine monohydrochloride. Stirring was continued for 4 hours at reflux temperature. The precipitate was filtered off (*), washed with pyridine, stirred in water and washed successively with water, 2-propanol and 2,2'-oxybispropane. The product was filtered off and dried in vacuo at 100° C., yielding a first fraction of 9.6 parts (57.1%) of product (E/Z=75/25); mp.>300° C. The filtrate (*) was evaporated and the residue was treated in the same manner as the precipitate hereinbefore, yielding an additional 5.5 parts (32.7%) of product. Total yield: 15.1 parts (89.8%) of (E+Z)-3,5-dihydro-7-[(hydroxyimino)phenylmethyl]imidazo[2,1-b]quinazolin-2(1H)-one (comp. 2).

EXAMPLE 18

A mixture of 2.01 parts of compound (2), 6 parts of 2-propanol, saturated with hydrochloric acid and 62 parts of 1,4-dioxane was stirred for 4 hours at room temperature. Gaseous hydrogen chloride was bubbled through the reaction mixture, while cooling in an ice-bath. Stirring was continued overnight at room temperature. The precipitate was filtered off, washed with 2,2'-oxybispropane and stirred in water. The aqueous layer was treated with an ammonium hydroxide solution and stirred for 10 min. The precipitate filtered off, washed with water and purified by column chromatography (HPLC; silica gel; H$_2$O/CH$_3$OH (0.5% (NH$_4$)$_2$CO$_3$)). The eluent of the desired fractions was evaporated and the residue was stirred in water. The product was filtered off, washed with water and dried in vacuo at 70°-90° C., yielding 0.867 parts (41.3%) of (E)-3,5-dihydro-7-[(hydroxyimino)phenylmethyl]imidazo[2,1-b]quinazolin-2(1H)-one; mp.>300° C. (comp. 3).

EXAMPLE 19 a) A mixture of 8.5 parts of compound (2), 110 parts of dimethyl sulfoxide, 8.36 parts of 1,1-dimethylethylchlorodimethylsilane and 7.56 parts of 1H-imidazole was stirred for 10 min at 60° C. The reaction mixture was poured into 500 parts of water and the whole was extracted with 2,2'-oxybispropane. The extract was dried, filtered and evaporated. The residue was crystallized from methanol, washed with methanol and dried, yielding a first fraction of 7.1 parts (60.9%) of product. Evaporation of the mother liquor yielded an additional 4.6 parts (39.5%) of product.

Total yield: 11.7 parts (≈100%) of (E+Z)-7-[[[(1,1-dimethylethyl)dimethylsiloxy]imino]phenylmethyl]-3,5-dihydroimidazo[2,1-b]quinazolin-2(1H)-one; mp. 254.7° C. (comp. 5).

b) Compound (5) was separated into its pure E and Z isomers by column chromatography (HPLC; silicagel γ-aminopropyl; (C$_2$H$_5$)$_2$O)/CH$_3$CN/THF/H$_2$O 46.5:5:46.5:2). The eluent of the separated E- and Z-isomer fractions was evaporated and the residues were chromatographed again (HPLC; γ-aminopropyl; CH$_2$Cl$_2$/CH$_3$OH 96:4). The products were dried in vacuo, yielding 3.3 parts (19.7%) of (E)-7-[[[[(1,1-dimethylethyl)dimethylsilyl]oxy]imino]phenylmethyl]-3,5-dihydroimidazo[2,1-b]quinazolin-2(1H)-one; mp. 221.0° C. (comp. 18) and 0.9 parts (5.4%) of (Z)-7-[[[[(1,1-dimethylethyl)dimethylsilyl]oxy]imino]phenylmethyl]-3,5-dihydroimidazo[2,1-b]-quinazolin-2(1H)-one; mp.>250° C. (decomp.) (comp. 19).

c) To a mixture of 0.103 parts of compound (19) and 4.45 parts of tetrahydrofuran there were added 0.53 parts of a solution of tetrabutylammonium fluoride in tetrahydrofuran 1M. After stirring for 10 min at room temperature, the reaction mixture was evaporated and the residue was taken up in water. The solid was filtered off, washed with water and boiled in methanol. The product was filtered off, washed with methanol and 2,2'-oxybispropane and dried in vacuo at 80° C., yielding 0.033 parts (35.9%) of (Z)-3,5-dihydro-7-[(hydroxyimino)phenylmethyl]imidazo[2,1-b]quinazolin-2(1H)-one; mp.>250° C. (comp. 15).

EXAMPLE 20 a) A solution of 0.3 parts of compound (6), 2.5 parts of a sodium hydroxide solution 1N and 2 parts of methanol was stirred for 1 hour at room temperature. There were added 2.5 parts of a hydrochloric acid solution 1N. The precipitated product was filtered off, washed with water and methanol and crystallized from methanol. The product was filtered off, washed with methanol and 2,2'-oxybispropane and dried in vacuo at 60° C., yielding 0.15 parts (53.7%) of (E+Z)-2-[[[phenyl(1,2,3,5-tetrahydro-2-oxoimidazo[2,1-b]quinazolin-7-yl)methylene]amino]oxy]acetic acid; mp. 253.0° C. (E/Z=75/25) (comp. 7).

b) Compound 56 was prepared from compound 37 in a similar manner, but without organic solvent (methanol) and with stirring at 60° C. for 1 hour.

EXAMPLE 21 a) A mixture of 10.7 parts of compound (28), 78.4 parts of a sodium hydroxide solution 1N and 59.3 parts of ethanol was stirred overnight at room temperature.

The aqueous layer was extracted with dichloromethane and then acidified to pH 5 with HCl 2N. The product was filtered off, washed with water, co-evaporated with a mixture of methanol and methylbenzene and with methylbenzene, boiled in methanol, washed with a mixture of methanol and 2,2'-oxybispropane and dried at 60° C., yielding 2.1 parts (21.4%) of (E+Z)-4-[[[phenyl(1,2,3,5-tetrahydro-2-oxoimidazo[2,1-b]quinazolin-7-yl)methylene]amino]oxy]butanoic acid; mp. 268.5° C. (comp. 31).

b) To a stirred solution of 1.9 parts of compound (31) in 303 parts of dimethyl sulfoxide there were added 1.5 parts of 1,1'-carbonylbis[1H-imidazole]. After stirring for 10 min at room temperature, for 2 hours at 60° C. and for ½ hour at 80° C., there were added 4.7 parts of N-methylcyclohexanamine. Stirring was continued overnight at 80° C. The reaction mixture was poured into water and the whole was acidified to pH 5 with acetic acid 10%. The product was extracted with dichloromethane and the extract was washed with water, dried, filtered and evaporated. The residue was purified twice by column chromatography (silica gel; CH₃COOC₂H₅/CH₃OH 95:5; CH₂Cl₂/CH₃OH 95:5). The eluent of the desired fraction was evaporated and the residue was co-evaporated with methylbenzene. The E and Z isomers were separated by HPLC (Licroprep amino; CHCl₃). The two fractions were evaporated and the residues stirred in water and dried in vacuo at 70° C., yielding 0.05 parts (2.1%) of (E)-N-cyclohexyl-N-methyl-4-[[[phenyl(1,2,3,5-tetrahydro-2-oxoimidazo[2,1-b]quinazolin-7-yl)methylene]amino]oxy]butanamide (comp. 33) and 0.03 parts (1.3%) of (Z)-N-cyclohexyl-N-methyl-4-[[[phenyl(1,2,3,5-tetrahydro-2-oxoimidazo[2,1-b]quinazolin-7-yl)methylene]amino]oxy]butanamide (comp. 34).

EXAMPLE 22

A mixture of 1.96 parts of intermediate (56), 20 parts of ammonium acetate and 2.1 parts of acetic acid was stirred for 45 min at 130° C. The reaction mixture was diluted with water. The precipitate was filtered off, stirred in N,N-dimethylformamide and methanol and was then dissolved in 20 ml of formic acid. After filtration, there was added tetrahydrofuran to enhance precipitation. The product was filtered off and dried in vacuo at 85° C., yielding 0.9 parts (56.0%) of 1,5-dihydro-7-(3-pyridinylcarbonyl)imidazo[2,1-b]quinazolin-2(3e,uns/H/ )-one; mp. 275.1° C. (comp. 39).

EXAMPLE 23

To a mixture of 1 part of compound (65) and 9.4 parts of N,N-dimethylformamide there were added dropwise 0.4 parts of thionyl chloride. After stirring for 5 min, there were added at once 2.03 parts of N-methylcyclohexanamine. The whole was stirred for 5 min and was then evaporated. The residue was stirred in water, filtered off and purified by column chromatography (silica gel; CHCl₃/CH₃OH 95:5). The eluent of the desired fraction was evaporated and the residue was crystallized from 2-propanol. The product was filtered off, washed with 2-propanol and 1,1'-oxybisethane and dried, yielding 0.4 parts (31.1%) of (E)-N-cyclohexyl-3-(1,2,3,5-tetrahydro-2-oxoimidazo[2,1-b]quinazolin-7-yl)-N-methyl-3-phenyl-2-propenamide; mp. 204° C. (decomp.) (comp. 67).

EXAMPLE 24 a) 133 Parts of dichloromethane were stirred while gaseous hydrochloric acid was bubbled through for 1 min. There were added portionwise 4.6 parts of compound (59) and gaseous hydrochloric acid was passed through for 1 more min. After the dropwise addition of 1.36 parts of thionyl chloride, the whole was stirred at reflux temperature for 40 min. The reaction mixture was evaporated and the residue was co-evaporated with methylbenzene, yielding 4.9 parts (94.0%) of (E+Z)-5-[[[phenyl(1,2,3,5-tetrahydro-2-oxoimidazo[2,1-b]quinazolin-7-yl)methylene]amino]oxy]pentanoyl chloride monohydrochloride (interm. 84).

b) To a stirred solution of 6.0 parts of N-methylcyclohexanamine and 160 parts of dichloromethane there were added portionwise 5.9 parts of intermediate (84). Stirring was continued for 1 hour at room temperature. The reaction mixture was poured into water and the product was extracted with dichloromethane. The extract was washed with water, dried, filtered and evaporated. The residue was purified by column chromatography (silica gel; CH₂Cl₂/CH₃OH 92.5:7.5) and then separated into its E and Z isomers by HPLC (silica gel; γ-aminopropyl; c.hexane/(C₂H₅)₂O/CH₃OH/H₂O 45:45:10:1). The E isomer fraction was crystallized from 2-propanol. The product was filtered off, washed with 2,2'-oxybispropane and dried in vacuo at 50° C., yielding 0.12 parts (1.81%) of (E)-N-cyclohexyl-N-methyl-5-[[[phenyl(1,2,3,5-tetrahydro-2-oxoimidazo[2,1-b]quinazolin-7-yl)methylene]amino]oxy]pentanamide; mp. 189.9° C. (comp. 61). The Z isomer fraction was stirred in 2,2'-oxybispropane. The product was filtered off, washed with 2,2'-oxybispropane and dried in vacuo at 40° C., yielding 0.42 parts (6.23%) of (Z)-N-cyclohexyl-N-methyl-5-[[[phenyl(1,2,3,5-tetrahydro-2-oxoimidazo[2,1-b]quinazolin-7-yl)methylene]amino]oxy]pentanamide hemihydrate; mp. 104.1° C. (comp. 60).

All compounds listed in Tables 1 and 2 were prepared following methods of preparation described in Examples 15-24, as is indicated in the column Ex. No.

TABLE 1

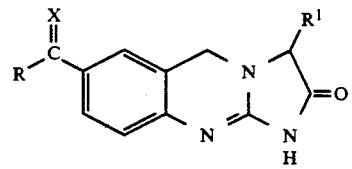

| Comp No. | Ex No. | R | X | R¹ | Physical Data |
|---|---|---|---|---|---|
| 1 | 15 | C₆H₅ | O | H | mp. >300° C. |
| 2 | 17 | C₆H₅ | NOH | H | (E + Z)/mp. >300° C. (dec.) |
| 3 | 18 | C₆H₅ | NOH | H | (E)/mp. 279.7° C. |
| 4 | 17 | C₆H₅ | NOCH₃ | H | (E + Z)/mp. 265.0° C. (dec.) |
| 5 | 19a | C₆H₅ | NOSi(CH₃)₂(t-C₄H₉) | H | (E + Z)/mp. 254.7° C. |

TABLE 1-continued

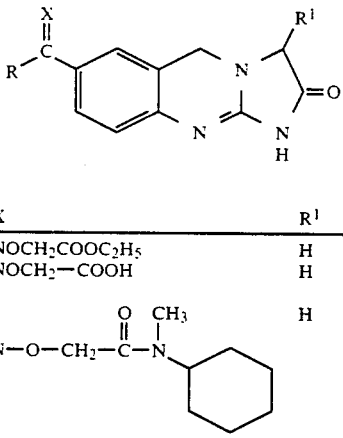

| Comp No. | Ex No. | R | X | R¹ | Physical Data |
|---|---|---|---|---|---|
| 6 | 16 | $C_6H_5$ | $NOCH_2COOC_2H_5$ | H | (E + Z)/mp. 251.7° C. |
| 7 | 20a | $C_6H_5$ | $NOCH_2-COOH$ | H | (E + Z)/mp. 253.0° C. |
| 8 | 16 | $C_6H_5$ | 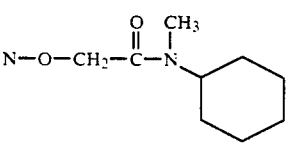 | H | (E + Z)/HCl/1/2(CH₃)₂CHOH mp. 169.8° C. |
| 9 | 16 | $C_6H_5$ | 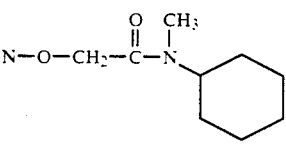 | H | (E)/mp. 202.2° C. |
| 10 | 16 | $C_6H_5$ | 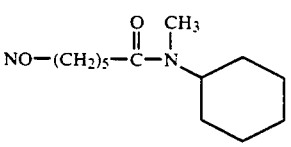 | H | (Z)/mp. 173.4° C. |
| 11 | 15 | $C_6H_5$ | O | $CH_3$ | mp. >300° C. |
| 12 | 15 | $4\text{-}CH_3O-C_6H_4$ | O | H | mp. 260° C. (dec.) |
| 13 | 17 | $4\text{-}CH_3O-C_6H_4$ | NOH | H | (E + Z)/1/2 H₂O mp. 290.8° C. |
| 14 | 15 | $4\text{-}F-C_6H_4$ | O | H | mp. >300° C. (dec.) |
| 15 | 19c | $C_6H_5$ | NOH | H | (Z)/mp. >250° C. |
| 16 | 17 | $4\text{-}Br-C_6H_4$ | NOH | H | (E + Z:55/45)/mp. >300° C. |
| 17 | 15 | $4\text{-}Br-C_6H_4$ | O | H | mp. >300° C. |
| 18 | 19b | $C_6H_5$ | $NOSi(CH_3)_2(t\text{-}C_4H_9)$ | H | (E)/mp. 221° C. |
| 19 | 19b | $C_6H_5$ | $NOSi(CH_3)_2(t\text{-}C_4H_9)$ | H | (Z)/mp. >250.0° C. |
| 20 | 15 | $4\text{-}CH_3-C_6H_4$ | O | H | mp. >300° C. (dec.) |
| 21 | 15 | $3\text{-}CH_3O-C_6H_4$ | O | H | mp. 280° C. |
| 22 | 17 | $4\text{-}F-C_6H_4$ | NOH | H | (E + Z)/mp. 274.2° C. |
| 23 | 17 | $4\text{-}CH_3-C_6H_4$ | NOH | H | (E + Z)/mp. 271.2° C. |
| 24 | 15 | $3,4\text{-}(CH_3O)_2C_6H_3$ | O | H | mp. >300° C. |
| 25 | 17 | $3\text{-}CH_3O-C_6H_4$ | NOH | H | (E + Z)/mp. >300° C. |
| 26 | 17 | $3,4\text{-}(CH_3O)_2C_6H_3$ | NOH | H | (E + Z)/mp. 216.6° C. |
| 27 | 15 | $4\text{-}Cl-C_6H_4$ | O | H | mp. 260° C. (dec.) |
| 28 | 16 | $C_6H_5$ | $NO(CH_2)_3COOC_2H_5$ | H | (E + Z)/mp. 190.0° C. |
| 29 | 17 | $4\text{-}Cl-C_6H_4$ | NOH | H | (E + Z)/1/2 H₂O/ mp. >300° C. (dec.) |
| 30 | 16 | $C_6H_5$ | 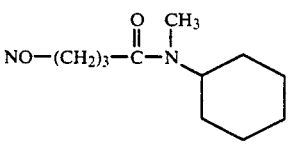 | H | (E)/mp. 151.2° C. |
| 31 | 21a | $C_6H_5$ | $NO-(CH_2)_3-COOH$ | H | (E + Z)/mp. 268.5° C. |
| 32 | 16 | $C_6H_5$ | $CH-COOC_2H_5$ | H | mp. 228.6° C. |
| 33 | 21b | $C_6H_5$ | 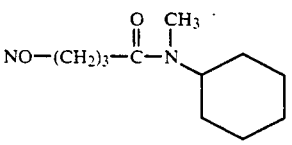 | H | (E) |
| 34 | 21b | $C_6H_5$ | 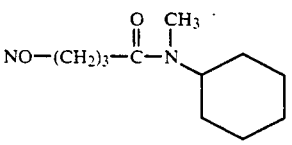 | H | (Z) |

TABLE 1-continued

Structure: R-C(=X)- attached to a benzene ring with a -CH₂-N group leading to an imidazolidinone ring (with R¹ substituent) containing N-H and C=O, connected via N=C.

| Comp No. | Ex No. | R | X | R¹ | Physical Data |
|---|---|---|---|---|---|
| 35 | 16 | 4-Br—C₆H₄ | NO—CH₂—C(=O)—N(CH₃)(cyclohexyl) | H | (E)/mp. 229.3° C. |
| 36 | 16 | C₆H₅ | NO(CH₂)₄COOC₂H₅ | H | (E + Z)/mp. 139.8° C. |
| 37 | 16 | C₆H₅ | NO(CH₂)₂COOC₂H₅ | H | (E + Z)/mp. 185.2° C. |
| 38 | 16 | 4-F—C₆H₄ | NO—CH₂—C(=O)—N(CH₃)(cyclohexyl) | H | (E)/3/2H₂O/mp. 205.6° C. |
| 39 | 22 | 3-pyridinyl | O | H | mp. 275.1° C. |
| 40 | 17 | 3-pyridinyl | NOH | H | (E + Z)/1/2H₂O/mp. 279.4° C. |
| 41 | 16 | 4-F—C₆H₄ | NO—CH₂—C(=O)—N(CH₃)(cyclohexyl) | H | (E + Z)/1/2H₂O/mp. 240.2° C. |
| 42 | 16 | 4-CH₃—C₆H₄ | NO—CH₂—C(=O)—N(CH₃)(cyclohexyl) | H | (E)/1/2H₂O/mp. 189.3° C. |
| 43 | 16 | 3-Br—C₆H₄ | NO—CH₂—C(=O)—N(CH₃)(cyclohexyl) | H | (E)/1/2H₂O/mp. 198.4° C. |
| 44 | 16 | 3-Br—C₆H₄ | NO—CH₂—C(=O)—N(CH₃)(cyclohexyl) | H | (Z)/1/2H₂O/mp. 200.0° C. |
| 45 | 16 | H | NO—CH₂—C(=O)—N(CH₃)(cyclohexyl) | H | (E)/mp. 241° C. |
| 46 | 16 | 4-Cl—C₆H₄ | NO—CH₂—C(=O)—N(CH₃)(cyclohexyl) | H | E/1/2H₂O/mp. 207.4° C. |

TABLE 1-continued

| Comp No. | Ex No. | R | X | R¹ | Physical Data |
|---|---|---|---|---|---|
| 47 | 16 | 4-CF$_3$—C$_6$H$_4$ | NO—CH$_2$—C(=O)—N(CH$_3$)(cyclohexyl) | H | Z/mp. 195.8° C. |
| 48 | 16 | 4-CF$_3$—C$_6$H$_4$ | NO—CH$_2$—C(=O)—N(CH$_3$)(cyclohexyl) | H | E/mp. 229.7° C. |
| 49 | 16 | 3-CH$_3$O—C$_6$H$_4$ | NO—CH$_2$—C(=O)—N(CH$_3$)(cyclohexyl) | H | Z/1/2H$_2$O/mp. 155.2° C. |
| 50 | 16 | 3-Cl—C$_6$H$_4$ | NO—CH$_2$—C(=O)—N(CH$_3$)(cyclohexyl) | H | Z/1/2H$_2$O/mp. 216.7° C. |
| 51 | 16 | 3-Cl—C$_6$H$_4$ | NO—CH$_2$—C(=O)—N(CH$_3$)(cyclohexyl) | H | E/1/2H$_2$O/mp. 189.4° C. |
| 52 | 16 | 3-CH$_3$O—C$_6$H$_4$ | NO—CH$_2$—C(=O)—N(CH$_3$)(cyclohexyl) | H | E/1/2H$_2$O/mp. 169.9° C. |
| 53 | 16 | 2-thienyl | NO—CH$_2$—C(=O)—N(CH$_3$)(cyclohexyl) | H | (E + Z)/mp. 204.9° C. |
| 54 | 16 | 3-CH$_3$—C$_6$H$_4$ | NO—CH$_2$—C(=O)—N(CH$_3$)(cyclohexyl) | H | E/H$_2$O/mp. 150.0° C. |
| 55 | 16 | 3-CH$_3$—C$_6$H$_4$ | NO—CH$_2$—C(=O)—N(CH$_3$)(cyclohexyl) | H | Z/1/2H$_2$O/mp. 161.0° C. |
| 56 | 20b | C$_6$H$_5$ | NO—(CH$_2$)$_2$COOH | H | (E + Z) |

TABLE 1-continued

[Structure: benzene ring with X=C(R) group at one position and CH₂-N-CH(R¹)-C(=O)-NH-C(=N)- imidazolinone fused system]

| Comp No. | Ex No. | R | X | R¹ | Physical Data |
|---|---|---|---|---|---|
| 57 | 24 | C₆H₅ | NO—(CH₂)₂—C(=O)—N(CH₃)(cyclohexyl) | H | Z/1/2H₂O/mp. 186.7° C. |
| 58 | 24 | C₆H₅ | NO—(CH₂)₂—C(=O)—N(CH₃)(cyclohexyl) | H | E/1/2H₂O/mp. 140.8° C. |
| 59 | 21a | C₆H₅ | NO—(CH₂)₄—COOH | H | (E + Z) |
| 60 | 24b | C₆H₅ | NO—(CH₂)₄—C(=O)—N(CH₃)(cyclohexyl) | H | Z/1/2H₂O/mp. 104.1° C. |
| 61 | 24b | C₆H₅ | NO—(CH₂)₄—C(=O)—N(CH₃)(cyclohexyl) | H | E/mp. 189.9° C. |

TABLE 2

[Structure: 6-benzoyl-substituted benzene fused with CH₂-N-C(R¹)(R²)-C(=O)-NH-C(=N)- imidazolinone ring system]

| Comp No. | Ex. No. | X | R¹ | R² | Physical Data |
|---|---|---|---|---|---|
| 62 | 16 | CHCOOC₂H₅ | H | H | (Z)/mp. 259.9° C. |
| 63 | 16 | CHCOOC₂H₅ | H | H | (E)/mp. 279.2° C. |
| 64 | 21a | CHCOOH | H | H | (Z)/mp. >300° C. |
| 65 | 21a | CHCOOH | H | H | (E)/ |
| 66 | 23 | CH—C(=O)—N(CH₃)(cyclohexyl) | H | H | (Z)/1/2H₂O/mp. 219.4° C. |
| 67 | 23 | CH—C(=O)—N(CH₃)(cyclohexyl) | H | H | (E)/mp. 204° C. |
| 68 | 15 | O | CH₂—CH₂ | | mp. >300° C. |
| 69 | 17 | NOH | CH₂—CH₂ | | (E + Z)/mp. >300° C. |
| 70 | 15 | O | CH₃ | CH₃ | mp. >300° C. |
| 71 | 17 | NOH | CH₃ | CH₃ | (E + Z)/mp. 295.0° C. |

C) Pharmacological examples

The positive inotropic and lusitropic effect of the instant compounds were assessed by an in vitro assay system to detect inhibiting effect on the phosphodiesterase type $III_c$ and in an in vivo experiment in closed-chest anaestetized dogs by monitoring cardiac and haemodynamic effects of an intravenous infusion of the instant compounds.

EXAMPLE 25

Inhibition of Phosphodiesterase type $III_c$ (PDE $III_c$).

The incubation mixture (pH 7.1) (200 μl) contained 50 mM 4-morpholinopropanesulfonic acid (MOPS), 1 mM ethylenebis(oxyethylenenitrilo)tetraacetic acid (EGTA), 6 mM magnesium chloride, 0.25 mg/ml bovine serum albumin, 1.2 μM $^3$H-cAMP (310 mCi/mmole) and the phosphodiesterase type $III_c$, and was prepared by dilution with water of a stock solution of MOPS, EGTA, $MgCl_2$, BSA and $^3$H-cAMP (50 μl) and 2 to 50 μl of a solution of phosphodiesterase type $III_c$, depending on the enzymatic activity. A protein concentration was chosen that showed a linear increase of phosphodiesterase activity during an incubation period of 10 minutes at 37° C.

When the effect of different compounds on phosphodiesterase activity was tested, the medium without cAMP was incubated with the compound(s) or its carrier (DMSO-1% final concentration) for 5 min. The enzymatic reaction was started by addition of $^3$H-cAMP and stopped 10 min later after transferring the tubes in a waterbath at 100° C. for 40 sec. After cooling to room temperature, alkaline phosphatase (0.25 μg/ml) was added and the mixture was left at room temperature for 20 min. The mixture was subsequently applied to a 1 ml DEAE-Sephadex A-25 column (pasteur pipet) and washed twice with 3 ml 20 mM Tris-HCl at pH 7.4. The $^3$H-labelled reaction products in the eluate were quantified by liquid scintillation counting.

The inhibiting effect of the present compounds on canine heart and human platelet phosphodiesterase PDE $III_c$ was measured at different concentrations of the instant compounds. The $IC_{50}$ values were calculated graphically from the thus obtained inhibition values. Table 3 shows available $IC_{50}$ values of the present compounds on canine heart and human platelet PDE $III_c$.

TABLE 3

| Comp. No. | Canine heart PDE $III_c$ $IC_{50}$ ($10^{-6}$ M) | Human Platelet PDE $III_c$ $IC_{50}$ ($10^{-6}$ M) |
| --- | --- | --- |
| 1 | 0.55 | — |
| 2 | 0.44 | 0.19 |
| 3 | 0.44 | 0.19 |
| 4 | 0.37 | — |
| 5 | 0.06 | — |
| 6 | 0.46 | 0.38 |
| 8 | 0.17 | 0.058 |
| 9 | 0.064 | 0.025 |
| 10 | 0.21 | 0.14 |
| 12 | 0.28 | — |
| 13 | 0.36 | — |
| 14 | 0.49 | 0.52 |
| 15 | 0.34 | — |
| 16 | 0.26 | — |
| 17 | 0.36 | — |
| 20 | 0.21 | — |
| 21 | 0.145 | — |
| 22 | 0.41 | — |
| 23 | 0.23 | — |
| 24 | 0.19 | 0.34 |
| 25 | 0.20 | — |
| 26 | 0.19 | — |

TABLE 3-continued

| | Comp. No. | Canine heart PDE $III_c$ $IC_{50}$ ($10^{-6}$ M) | Human Platelet PDE $III_c$ $IC_{50}$ ($10^{-6}$ M) |
| --- | --- | --- | --- |
| | 27 | 0.30 | — |
| | 28 | 0.22 | — |
| | 29 | 0.19 | — |
| | 30 | 0.14 | — |
| | 31 | 0.62 | — |
| | 32 | 0.26 | 0.084 |
| | 33 | 0.047 | — |
| | 34 | 0.78 | — |
| | 35 | 0.051 | — |
| | 36 | 0.09 | — |
| | 37 | 0.12 | — |
| | 38 | 0.076 | — |
| R 85.906 | 40 | 0.93 | — |
| R 86.134 | 41 | 0.12 | — |
| R 86.260 | 42 | 0.081 | — |
| R 86.313 | 43 | 0.15 | — |
| R 86.282 | 44 | 0.045 | — |
| R 86.251 | 45 | 0.025 | — |
| R 86.275 | 46 | 0.067 | — |
| R 86.325 | 48 | 0.74 | — |
| R 86.388 | 49 | 0.041 | — |
| R 86.620 | 52 | 0.04 | — |
| R 86.662 | 53 | 0.01 | — |
| R 86.756 | 54 | 0.15 | — |
| R 86.759 | 55 | 0.089 | — |
| R 86.838 | 57 | 0.15 | — |
| R 86.839 | 58 | 0.05 | — |
| R 86.856 | 60 | 0.24 | — |
| R 86.847 | 61 | 0.1 | — |
| R 86.033 | 62 | 0.49 | — |
| R 86.130 | 63 | 0.38 | — |
| R 86.399 | 65 | 0.65 | — |
| R 86.400 | 67 | 0.39 | — |

— = not yet tested

EXAMPLE 26

Positive inotropy and lusitropy, blood pressure and heart rate in dogs.

Compound (9) was dissolved in 20% hydroxypropyl beta cyclodextrine ether slightly acidified with 1N HCl, in a concentration of 1 mg.ml$^{-1}$ (pH 5.5). The experiments were performed on 7 mongrel dogs of either sex and varying age, ranging in body weight from 27 to 33 kg (median 30 kg). The animals were intravenously anaesthetized with a mixture of 0.015 mg.kg$^{-1}$ scopolamine and 0.05 mg.kg$^{-1}$ lofentanil. The animals were intubated with a cuffed endotracheal tube. Intermittent positive pressure ventilation was performed with a mixture of pressurized air and oxygen (60/40), using a volume-controlled ventilator (Siemens Elema). In the control period the $CO_2$ concentration in the expired air (ET $CO_2$), as determined with a capnograph (Gould Godart), was kept at 5 vol % by adjustment of the respiratory volume (resp. rate=20 breaths,min$^{-1}$). A continuous intravenous infusion of 0.5 mg.kg$^{-1}$.h$^{-1}$ of etomidate was started immediately after induction. Body temperature was monitored with a thermistor positioned in the pulmonary artery. To prevent blood clotting heparine, 1000 IU.kg$^{-1}$ i.v., was administered.

The electrocardiogram (ECG) was derived from limb leads (standard lead 2). Left ventricular (LVP) and ascending aortic blood pressure (AoP) were measured by retrograde catheterisation via the femoral arteries with high fidelity cathetertip micromanometers (Honeywell). The other femoral vein was cannulated for injection of saline at room temperature into the right atrium and for injection of compound (9). Peak ascending aortic blood flow velocity was measured through the right carotid artery with an electromagnetic catheter-tip probe connected to a square wave electromagnetic flow meter (Janssen Scientific Instruments). The following variables -inter alia-were calculated on-line, usually at 1 min intervals: heart rate (HR), diastolic (AoPd) aortic blood pressure, left ventricular end-diastolic pressure (LVEDP), the maximum positive and maximum negative rate of change of isovolumic LVP (LV dp/dt$_{max}$ and $_{min}$, respectively), the maximum positive first derivative divided by the actually developed pressure in the left ventricle (LV dp/dt$_{max}$/Pd). The time constant (T) of relaxation was measured with the use of an exponential analysis that also estimated the asymptote. After a recorded control period of 20 min the intravenous infusion of compound (9) was started at a rate of 0.005 mg.kg$^{-1}$ over 120 min. In the wash-out period the effects were followed for 75 min.

Compound (9) has positive inotropic properties, starting after 10 min of infusion (0.05 mg.kg$^{-1}$ total dose), as indicated by the pronounced and significant increase in the variables related to cardiac performance (LV dp/dt$_{max}$, LV dp/dt$_{max}$/Pd), in the presence of no change or even a slight decrease in left ventricular end-diastolic pressure (preload) and no change in heart rate. Compound (9) has positive lusitropic properties, as evidenced by the significant decrease in the time constant of relaxation starting after 10 min of infusion (0.05 mg.kg$^{-1}$ total dose). Systemic and pulmonary peripheral vascular resistance decrease significantly starting after 20 min of infusion of the compound (0.10 mg.kg$^{-1}$ total dose). This indicates that compound (9) has also additional systemic and pulmonary vasodilatory properties. This unloading of the heart occurs without altering heart rate, but with concomitant increase in cardiac output. These positive inotropic and lusitropic, and vasodilatory effects of the compound (9) are long-lasting, since the changes in the variables last for more than 75 min after stopping the infusion of a total dose of 0.60 mg.kg$^{-1}$.

following the same procedure, a dose-related increase in cardiac inotropy and lusitropy associated with a dose-related systemic vasodilation and an increase in cardiac output, without changing the heart rate, was observed upon slow infusion (0.005 mg kg$^{-1}$ min$^{-1}$) of compound (3) for two hours and lasted for more than 90 minutes after stopping the infusion.

Table 4 shows the % changes in haemodynamic variables measured after cumulative intravenous bolus administration of some of the present compounds in mongrel dogs (maximum end-dose is shown in mg kg$^{-1}$). The variable AoPd (diastolic aortic blood pressure) shows the decrease in blood pressure (vasodilation), HR the influence of the present compounds on the heart rate, LV dp/dt$_{max}$/Pd (the maximum positive rate of change of isovolumic left ventricular pressure divided by the actually developed pressure in the left ventricle) shows the positive inotropic effect and T (decrease in the time constant of relaxation) is a measure for positive lusitropy.

TABLE 4

| Comp. No. | % changes in haemodynamic variables | | | | end-dose mg kg$^{-1}$ |
|---|---|---|---|---|---|
| | AoPd | HR | LVdp/dt$_{max}$/Pd | T | |
| 2 | −10 | 15 | 102 | −38 | 0.16 |
| 6 | −13 | 9 | 31 | −15 | 0.16 |
| 11 8 | 0 | 0 | 29 | −45 | 0.16 |
| 10 | −5 | 0 | 18 | −13 | 0.16 |
| 12 | 0 | 10 | 57.5 | −10 | 0.16 |

TABLE 4-continued

| Comp. No. | % changes in haemodynamic variables | | | | end-dose mg kg$^{-1}$ |
|---|---|---|---|---|---|
| | AoPd | HR | LVdp/dt$_{max}$/Pd | T | |
| 13 | 0 | −10 | 45 | −27 | 0.16 |
| 14 | 0 | 5 | 35 | −16 | 0.08 |

D. Composition examples

The following formulations exemplify typical pharmaceutical compositions in dosage unit form suitable for systemic or topical administration to warm-blooded animals in accordance with the present invention.

"Active ingredient" (A.I.) as used throughout these examples relates to a compound of formula (I), a pharmaceutically acceptable acid addition salt or a stereochemically isomeric form thereof.

EXAMPLE 27

Oral drops 500 g of the A.I. is dissolved in 0.5 l of 2-hydroxypropanoic acid and 1.5 l of the polyethylene glycol at 60°-80° C. After cooling to 30°-40° C. there are added 35 l of polyethylene glycol and the mixture is stirred well. Then there is added a solution of 1750 g of sodium saccharin in 2.5 l of purified water and while stirring there are added 2.5 l of cocoa flavor and polyethylene glycol q.s. to a volume of 50 l, providing an oral drop solution comprising 10 mg/ml of the A.I. The resulting solution is filled into suitable containers.

EXAMPLE 28

Oral solution 9 g of methyl 4-hydroxybenzoate and 1 g of propyl 4-hydroxybenzoate are dissolved in 4 l of boiling purified water. In 3 l of this solution are dissolved first 10 g of 2,3-dihydroxybutanedioic acid and thereafter 20 g of the A.I. The latter solution is combined with the remaining part of the former solution and 12 l of 1,2,3-propanetriol and 3 l of sorbitol 70% solution are added thereto. 40 g of sodium saccharin are dissolved in 0.5 l of water and 2 ml of raspberry and 2 ml of gooseberry essence are added. The latter solution is combined with the former, water is added q.s. to a volume of 20 l providing an oral solution comprising 5 mg of the A.I. per teaspoonful (5 ml). The resulting solution is filled in suitable containers.

EXAMPLE 29

Capsules 20 g of the A.I., 6 g sodium sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 20 mg of the A.I.

EXAMPLE 30

Film-coated tablets

Preparation of tablet core

A mixture of 100 g of the A.I., 570 g lactose and 200 g starch is mixed well and thereafter humidified with a solution of 5 g sodium dodecyl sulfate and 10 g polyvinylpyrrolidone (Kollidon-K 90 ®) in about 200 ml of water. The wet powder mixture is sieved, dried and sieved again. Then there are added 100 g microcrystalline cellulose (Avicel ®) and 15 g hydrogenated vegetable oil (Sterotex ®). The whole is mixed well and compressed into tablets, giving 10.000 tablets, each comprising 10 mg of the active ingredient.

Coating

To a solution of 10 g methyl cellulose (Methocel 60 HG ®) in 75 ml of denaturated ethanol there is added a solution of 5 g of ethyl cellulose (Ethocel 22 cps ®) in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinylpyrrolidone and 30 ml of concentrated colour suspension (Opaspray K-1-2109 ®) and the whole is homogenated. The tablet cores are coated with the thus obtained mixture in a coating apparatus.

EXAMPLE 31

Injectable solution 1.8 g methyl 4-hydroxybenzoate and 0.2 g propyl 4-hydroxybenzoate are dissolved in about 0.5 l of boiling water for injection. After cooling to about 50° C. there are added while stirring 4 g lactic acid, 0.05 g propylene glycol and 4 g of the A.I. The solution is cooled to room temperature and supplemented with water for injection q.s. ad 1 l volume, giving a solution of 4 mg A.I. per ml. The solution is sterilized by filtration (U.S.P. XVII p. 811) and filled in sterile containers.

EXAMPLE 32

Suppositories 3 g A.I. is dissolved in a solution of 3 g 2,3-dihydroxybutanedioic acid in 25 ml polyethylene glycol 400. 12 g surfactant (SPAN ®) and triglycerides (Witepsol 555 ®) q.s. ad 300 g are molten together. The latter mixture is mixed well with the former solution. The thus obtained mixture is poured into moulds at a temperature of 37°-38° C. to form 100 suppositories each containing 30 mg of the A.I.

EXAMPLE 33

Injectable solution 60 g of A.I. and 12 g of benzylalcohol are mixed well and sesame oil is added q.s. ad 1 l, giving a solution comprising 60 mg/ml of A.I. The solution is sterilized and filled in sterile containers.

EXAMPLE 34

Injectable solution 350 g of hydroxypropyl-β-cyclodextrin is dissolved in 2.8 l of water. There are added successively 80.5 g of hydrochloric acid 0.1N and 1.75 g of (E)-N-cyclohexyl-N-methyl-2-[[[phenyl-(1,2,3,5-tetrahydro-2-oxoimidazo[2,1-b]-quinazolin-7-yl)methylene]-amino]oxy]acetamide. The whole is stirred until a clear solution is obtained and then the acidity is adjusted with sodium hydroxide 1N to pH 6. The solution is diluted with water to 3.5 l, thus yielding an injectable solution containing 0.5 mg/ml of A.I.

We claim:

1. A compound having the formula

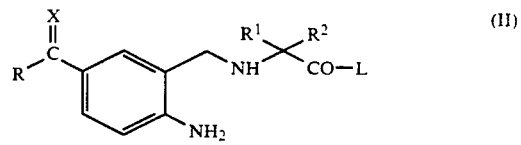

a pharmaceutically acceptable addition salt thereof or a stereochemically isomeric form thereof, wherein R is hydrogen, $C_{1-6}$alkyl, phenyl optionally substituted with from 1 to 3 substituents each independently selected from halo, hydroxy, $C_{1-6}$alkyloxy, $C_{1-6}$alkyl or trifluoromethyl; pyridinyl; or thienyl optionally substituted with halo or $C_{1-6}$alkyl;

$R^1$ is hydrogen or $C_{1-6}$alkyl;

$R^2$ is hydrogen, $C_{1-6}$alkyl, hydroxy$C_{1-6}$alkyl or phenyl; or $R^1$ and $R^2$ taken together may also form a $C_{1-5}$alkanediyl radical;

X is a radical of formula

 (a),

 (b), or

 (c):

$R^3$ is hydrogen, tri($C_{1-6}$alkyl)silyl or $C_{1-6}$alkyl optionally substituted with COOH, COO$C_{1-4}$alkyl, CONR$^5$R$^6$ or COOCH$_2$CONR$^7$R$^8$;

$R^4$ is COOH, COO$C_{1-4}$alkyl, CONR$^5$R$^6$, COOCH$_2$CONR$^7$R$^8$ or $C_{1-6}$alkyl optionally substituted with COOH, COO$C_{1-4}$alkyl, CONR$^5$R$^6$ or COOCH$_2$CONR$^7$R$^8$;

$R^5$ is hydrogen, $C_{1-4}$alkyl, hydroxy$C_{1-4}$alkyl, $C_{1-4}$alkyloxy$C_{1-4}$alkyl, hydroxycarbonyl$C_{1-4}$alkyl, $C_{1-4}$alkyloxycarbonyl$C_{1-4}$alkyl;

$R^6$ is hydrogen, $C_{1-4}$alkyl, hydroxy$C_{1-4}$alkyl or $C_{3-7}$cycloalkyl; or $R^5$ and $R^6$ taken together with the nitrogen atom to which they are attached may form a pyrrolidinyl, morpholinyl or piperazinyl ring, said piperazinyl ring being optionally substituted on the nitrogen atom with $C_{1-4}$alkyl or hydroxy$C_{1-4}$alkyl;

$R^7$ and $R^8$ each independently are hydrogen, $C_{1-4}$alkyl or hydroxy$C_{1-4}$alkyl; and L is a reactive leaving group.

* * * * *